United States Patent
Stewart et al.

(10) Patent No.: US 6,572,612 B2
(45) Date of Patent: Jun. 3, 2003

(54) ABLATION CATHETER AND METHOD FOR ISOLATING A PULMONARY VEIN

(75) Inventors: Mark T. Stewart, Lino Lakes, MN (US); William J. Flickinger, Lino Lakes, MN (US); David E. Francischelli, Anoka, MN (US); Rahul Mehra, Stillwater, MN (US); Xiaoyi Min, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/975,789

(22) Filed: Oct. 11, 2001

(65) Prior Publication Data

US 2002/0022839 A1 Feb. 21, 2002

Related U.S. Application Data

(63) Continuation of application No. 09/286,048, filed on Apr. 5, 1999, now Pat. No. 6,325,797.

(51) Int. Cl.[7] .............................................. A61B 18/14
(52) U.S. Cl. ........................ 606/41; 607/99; 607/113; 607/122
(58) Field of Search ...................... 606/41, 49; 607/99, 607/113, 122; 600/374, 381

(56) References Cited

U.S. PATENT DOCUMENTS

| | | | |
|---|---|---|---|
| 5,318,525 A | 6/1994 | West et al. | |
| 5,354,297 A | 10/1994 | Avitall | |
| 5,397,304 A | 3/1995 | Truckai | |
| 5,462,545 A | 10/1995 | Wang et al. | |
| 5,487,385 A | 1/1996 | Avitall | |
| 5,497,774 A | 3/1996 | Swartz et al. | |
| 5,545,193 A | 8/1996 | Fleishman et al. | |
| 5,545,200 A | 8/1996 | West et al. | |
| 5,549,661 A | 8/1996 | Kordis et al. | |
| 5,564,440 A | 10/1996 | Swartz et al. | |
| 5,575,766 A | 11/1996 | Swartz et al. | |
| 5,575,810 A | 11/1996 | Swanson et al. | |
| 5,582,609 A | 12/1996 | Swanson et al. | |
| 5,617,854 A | 4/1997 | Munsif | |
| 5,637,090 A | 6/1997 | McGee et al. | |
| 5,680,860 A | 10/1997 | Imran | |
| 5,687,723 A | 11/1997 | Avitall | |
| 5,690,611 A | 11/1997 | Swartz et al. | |
| 5,715,818 A | 2/1998 | Swartz et al. | |
| 5,725,512 A | 3/1998 | Swartz et al. | |
| 5,730,127 A | 3/1998 | Avitall | |
| 5,755,760 A | 5/1998 | Maguire et al. | |
| 5,814,028 A | 9/1998 | Swartz et al. | |
| 5,823,955 A | 10/1998 | Kuck et al. | |
| 5,842,984 A | 12/1998 | Avitall | |
| 5,860,974 A | * 1/1999 | Abele | 606/41 |
| 5,938,694 A | 8/1999 | Jaraczewski et al. | |
| 6,012,457 A | * 1/2000 | Lesh | 128/898 |
| 6,164,283 A | * 12/2000 | Lesh | 128/898 |
| 6,214,002 B1 | * 4/2001 | Fleishman et al. | 600/374 |

* cited by examiner

*Primary Examiner*—Lee Cohen
(74) *Attorney, Agent, or Firm*—Girma Wolds-Michael; Paul H. McDovall

(57) ABSTRACT

A catheter assembly and method for treatment of cardiac arrhythmia, for example, atrial fibrillation, by electrically isolating a vessel, such as a pulmonary vein, from a chamber, such as the left atrium. The catheter assembly includes a catheter body and at least one electrode. The catheter body includes a proximal portion, an intermediate portion and a distal portion. The intermediate portion extends from the proximal portion and defines a longitudinal axis. The distal portion extends from the intermediate portion and forms a substantially closed loop transverse to the longitudinal axis. The at least one electrode is disposed along the loop. With this configuration, the loop is axially directed into contact with the chamber wall about the vessel ostium. Upon energization, the electrode ablates a continuous lesion pattern about the vessel ostium, thereby electrically isolating the vessel from the chamber.

26 Claims, 11 Drawing Sheets

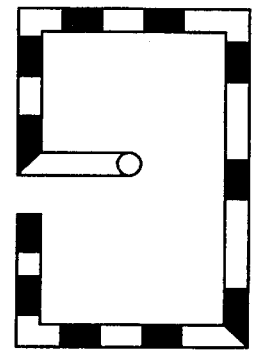
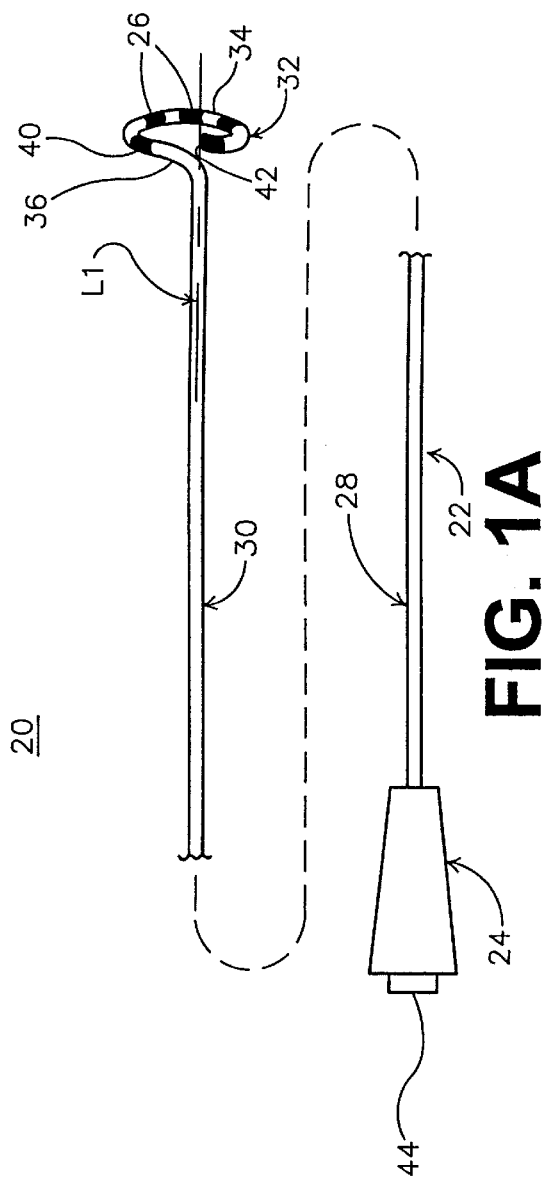
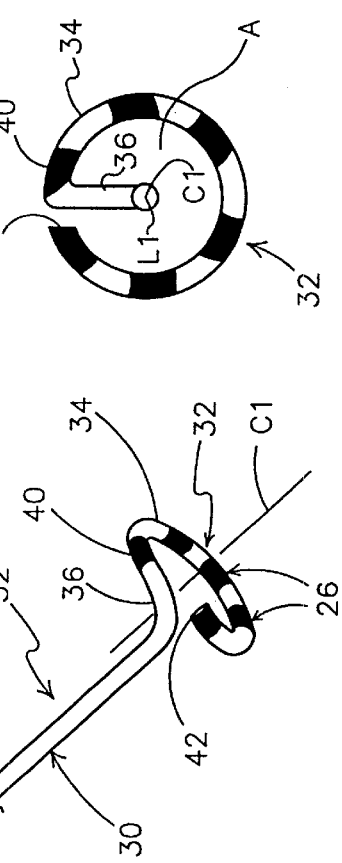

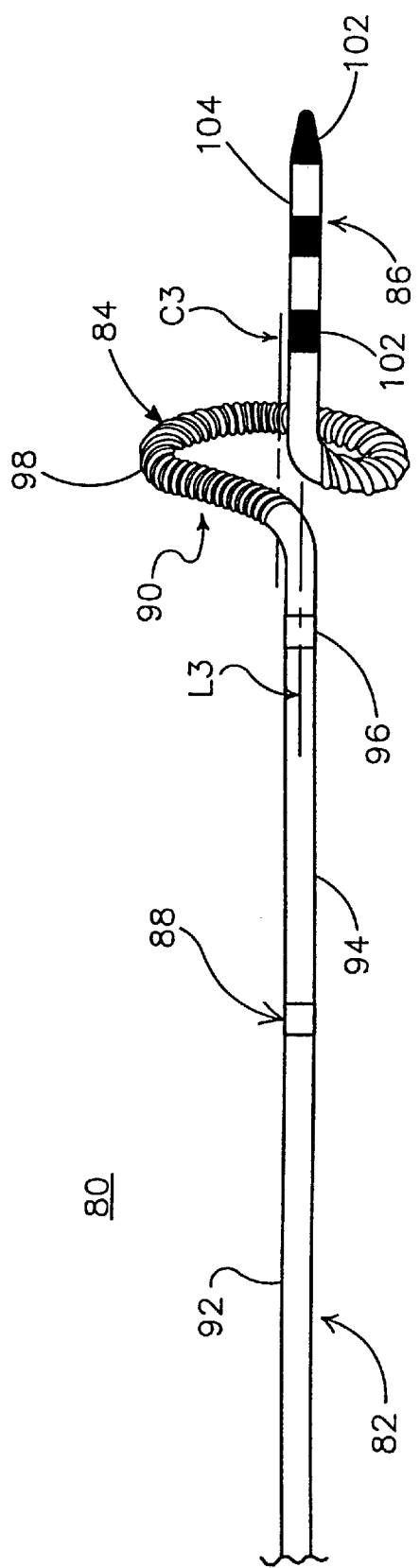
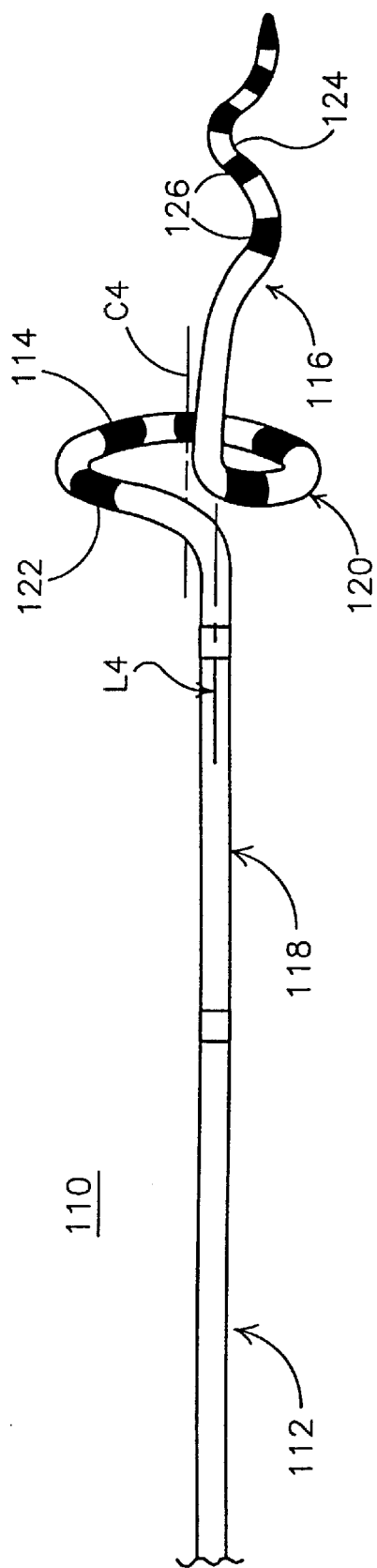
FIG. 4A
FIG. 5

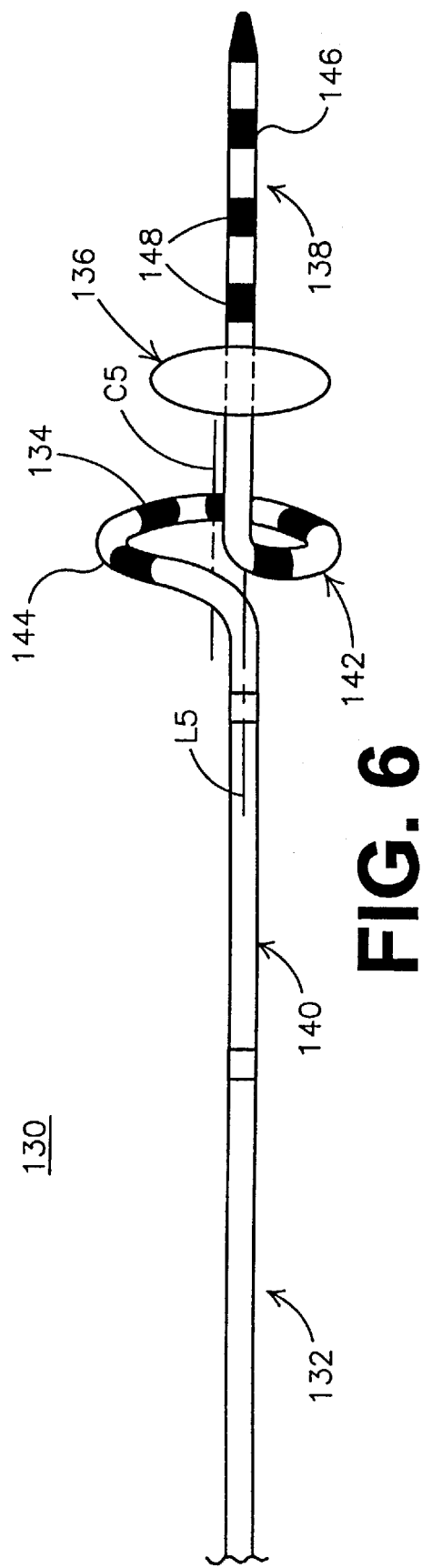
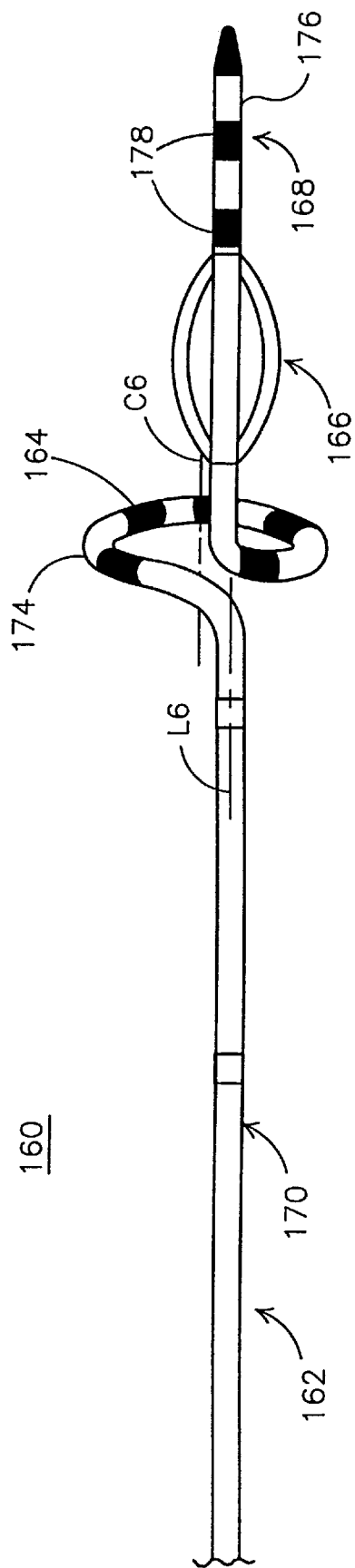

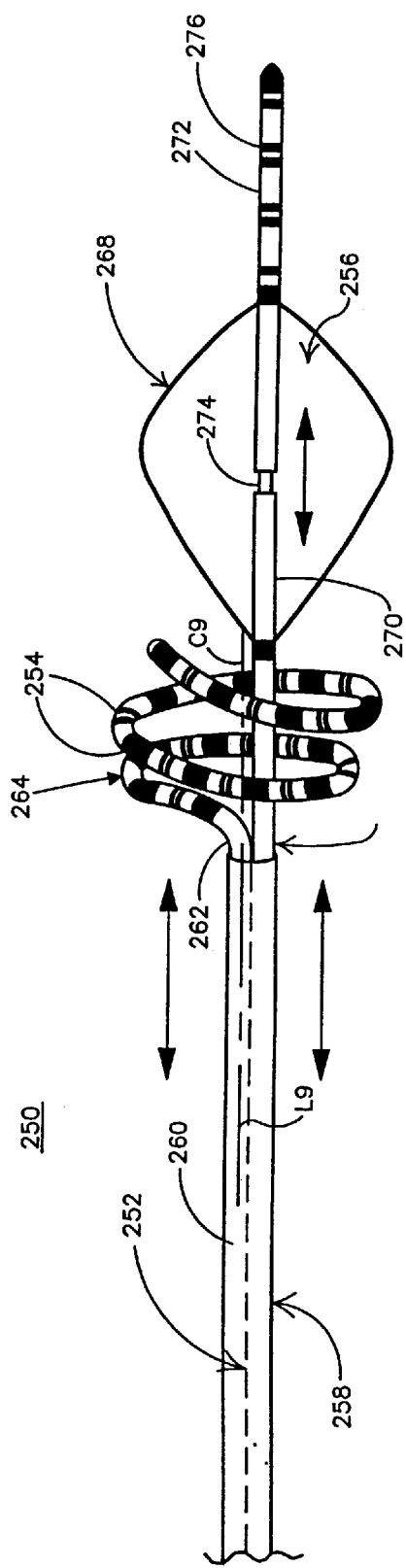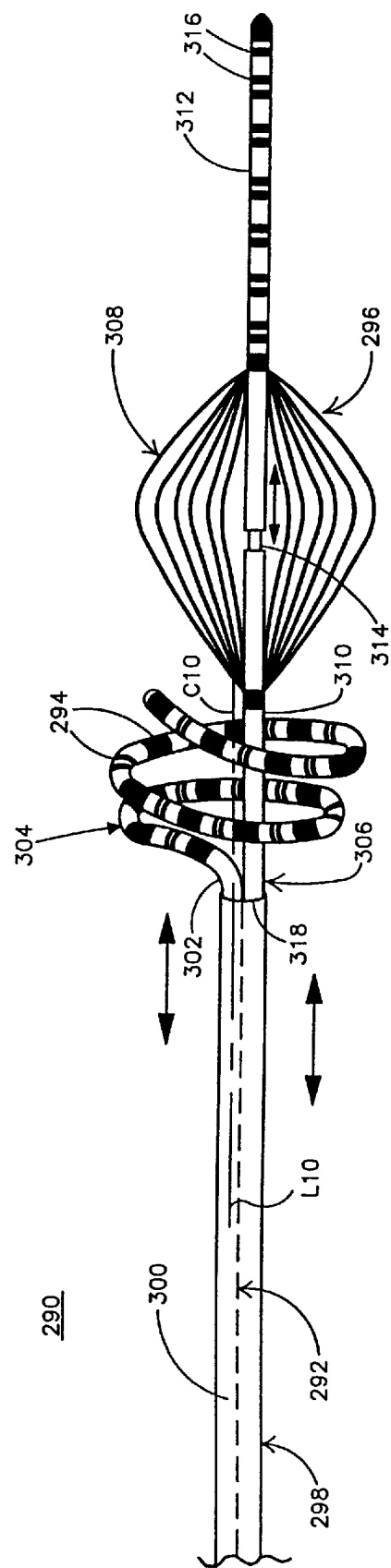

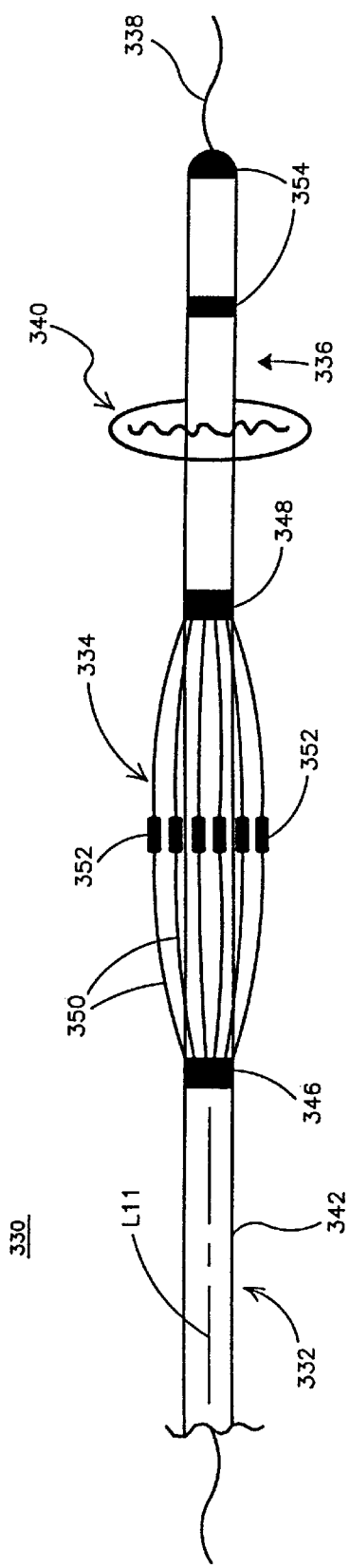
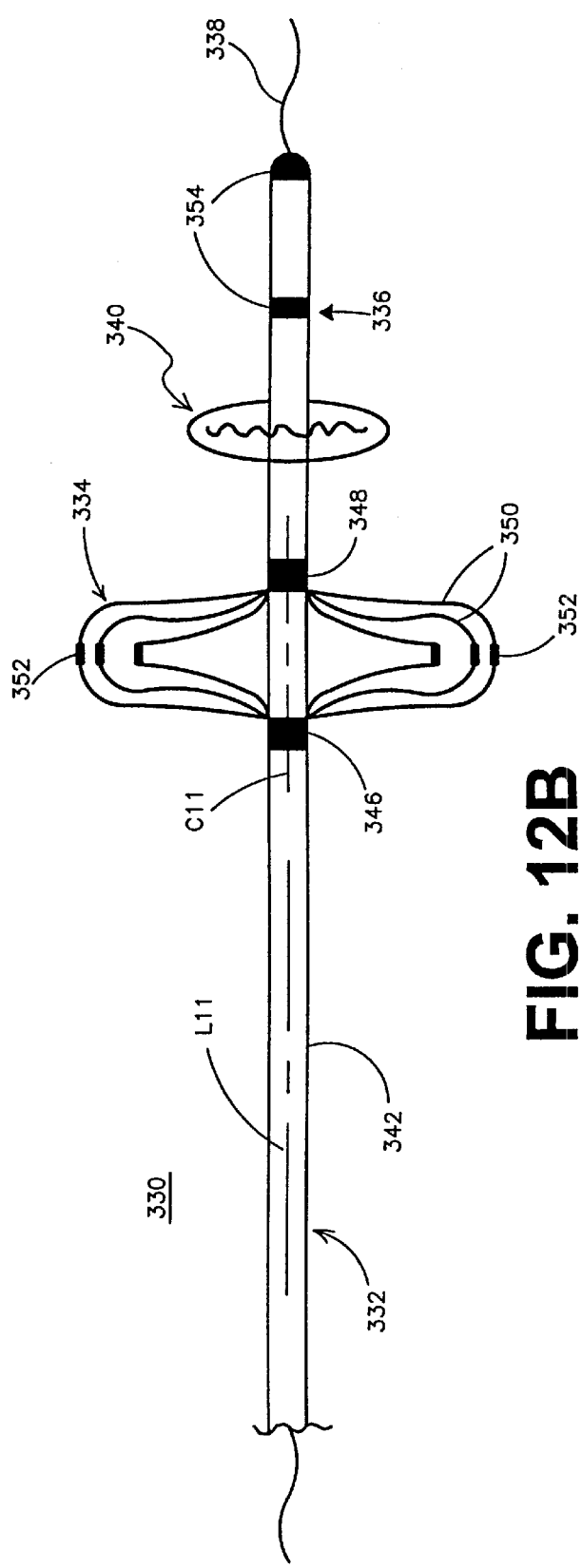

ABLATION CATHETER AND METHOD FOR ISOLATING A PULMONARY VEIN

This application is a division of patent application of application Ser. No. 09/286,048, filed Apr. 5, 1999, now U.S. Pat. No. 6,325,797.

BACKGROUND OF THE INVENTION

The present invention relates to an ablation catheter for treatment of cardiac arrhythmia, for example atrial fibrillation. More particularly, it relates to an ablation catheter configured to electrically isolate a vessel, such as a pulmonary vein, from a chamber, such as the left atrium with a continuous lesion pattern and a method for forming such a lesion pattern.

The heart includes a number of pathways that are responsible for the propagation of signals necessary to produce continuous, synchronized contractions. Each contraction cycle begins in the right atrium where a sinoatral node initiates an electrical impulse. This impulse then spreads across the right atrium to the left atrium, stimulating the atria to contract. The chain reaction continues from the atria to the ventricles by passing through a pathway known as the atrioventricular (AV) node or junction, which acts as an electrical gateway to the ventricles. The AV junction delivers the signal to the ventricles while also slowing it, so the atria can relax before the ventricles contract.

Disturbances in the heart's electrical system may lead to various rhythmic problems that can cause the heart to beat irregularly, too fast or too slow. Irregular heart beats, or arrhythmia, are caused by physiological or pathological disturbances in the discharge of electrical impulses from the sinoatrial node, in the transmission of the signal through the heart tissue, or spontaneous, unexpected electrical signals generated within the heart. One type of arrhythmia is tachycardia, which is an abnormal rapidity of heart action. There are several different forms of atrial tachycardia, including atrial fibrillation and atrial flutter. With atrial fibrillation, instead of a single beat, numerous electrical impulses are generated by depolarizing tissue at one or more locations in the atria (or possibly other locations). These unexpected electrical impulses produce irregular, often rapid heartbeats in the atrial muscles and ventricles. Patients experiencing atrial fibrillation may suffer from fatigue, activity intolerance, dizziness and even strokes.

The precise cause of atrial fibrillation, and in particular the depolarizing tissue causing "extra" electrical signals, is currently unknown. As to the location of the depolarizing tissue, it is generally agreed that the undesired electrical impulses often originate in the left atrial region of the heart. Recent studies have expanded upon this general understanding, suggesting that nearly 90% of these "focal triggers" or electrical impulses are generated in one (or more) of the four pulmonary veins (PV) extending from the left atrium. In this regard, as the heart develops from an embryotic stage, left atrium tissue may grow or extend a short distance into one or more of the PVs. It has been postulated that this tissue may spontaneously depolarize, resulting in an unexpected electrical impulse(s) propagating into the left atrium and along the various electrical pathways of the heart.

A variety of different atrial fibrillation treatment techniques are available, including drugs, surgery, implants, and catheter ablation. While drugs may be the treatment of choice for some patients, drugs typically only mask the symptoms and do not cure the underlying cause. Implantable devices, on the other hand, usually correct an arrhythmia only after it occurs. Surgical and catheter-based treatments, in contrast, will actually cure the problem by ablating the abnormal tissue or accessory pathway responsible for the atrial fibrillation. The catheter-based treatments rely on the application of various destructive energy sources to the target tissue, including direct current electrical energy, radiofrequency electrical energy, laser energy, and the like. The energy source, such as an ablating electrode, is normally disposed along a distal portion of a catheter.

Most ablation catheter techniques employed to treat atrial fibrillation focus upon locating the ablating electrode, or a series of ablating electrodes, along extended target sections of the left atrium wall. Because the atrium wall, and thus the targeted site(s), is relatively tortuous, the resulting catheter design includes multiple curves, bends, extensions, etc. In response to recent studies indicating that the unexpected electrical impulses are generated within a PV, efforts have been made to ablate tissue within the PV itself. Obviously, the prior catheter designs incorporating convoluted, multiple bends are not conducive to placement within a PV. Instead, a conventional "straight ended" ablation catheter has been employed. While this technique of tissue ablation directly within a PV has been performed with relatively high success, other concerns may arise.

More particularly, due to the relatively small thickness of atrial tissue formed within a PV, it is likely that ablation of this tissue may in fact cause the PV to shrink or constrict. Because PV's have a relatively small diameter, a stenosis may result. Even further, other vital bodily structures are directly adjacent each PV. These structures may be undesirably damaged when ablating within a PV.

In light of the above, an alternative technique has been suggested whereby a continuous ablation lesion pattern is formed in the left atrium wall about the ostium associated with the PV in question. In other words, the PV is electrically isolated from the left atrium by forming an ablation lesion pattern that surrounds the PV ostium. As a result, any undesired electrical impulse generated within the PV could not propagate into the left atrium, thereby eliminating unexpected atria contraction.

Unfortunately, while PV isolation via a continuous ablation lesion pattern about the PV ostium appears highly viable, no acceptable ablation catheter configuration exists. Most atrial fibrillation ablation catheters have linear distal ends, designed for manipulation in a sliding fashion along the atrial wall. That is to say, the distal, electrode-carrying end of the catheter is typically slid along (or parallel to) the atrial wall. With this generally accepted configuration in mind, it may be possible to shape the distal, electrode-carrying end into a small ring sized in accordance with the PV ostium. For example, U.S. Pat. No. 5,617,854 discloses one such possibility. More particularly, the described ablation catheter includes a substantially ring-shaped portion sized to contact the ostium of the coronary sinus. Pursuant to conventional designs, the ring extends linearly from the catheter body. In theory, the ring-shaped portion may be placed about a PV ostium. However, proper positioning would be extremely difficult and time consuming. More particularly, it would be virtually impossible to locate and then align the ring about a PV ostium when sliding the catheter along the atrium wall. The ring must be directed toward the ostium in a radial direction (relative to a central axis of the ostium). Even if the electrophysiologist were able to direct the ring to the ostium, the periodic blood flow through the PV would likely force the ring away from the atrium wall, as the catheter body would not provide any support.

A related concern entails mapping of a PV prior to ablation. In cases of atrial fibrillation, it is necessary to identify the origination point of the undesired electrical impulses prior to ablation. Thus, it must first be determined if the electrical impulse originates within one or more PVs. Once the depolarizing tissue has been identified, necessary ablation steps can be taken. Mapping is normally accomplished by placing one or more mapping electrodes into contact with the tissue in question. In order to map tissue within a PV, therefore, a relatively straight catheter section maintaining two or more mapping electrodes must be extended axially within the PV. Ablation catheters configured to slide along the atrial wall cannot include a separate, distal extension for placement within the PV. Instead, an entirely separate mapping catheter must be provided and then removed for subsequent replacement with the ablation catheter. Obviously, these additional steps greatly increase the overall time required to complete the procedure.

Electrical isolation of a pulmonary vein via an ablation lesion pattern surrounding the pulmonary vein ostium presents a potentially revolutionary technique for treatment of atrial fibrillation. However, the unique anatomical characteristics of a pulmonary vein and left atrium render currently available ablation catheters minimally useful. Therefore, a substantial need exists for an ablation catheter designed for consistent positioning of one or more ablation electrodes about a pulmonary vein ostium, as well as for providing pulmonary vein mapping information.

SUMMARY OF THE INVENTION

One aspect of the present invention provides a catheter assembly for treatment of cardiac arrhythmia. The catheter assembly includes a catheter body and at least one electrode. The catheter body includes a proximal portion, an intermediate portion and a distal portion. The intermediate portion extends from the proximal portion and defines a longitudinal axis. The distal portion extends from the intermediate portion and forms a substantially closed loop transverse to the longitudinal axis. The electrode is disposed along the loop. With this configuration, upon activation, the electrode ablates a continuous lesion pattern in a plane substantially perpendicular to the longitudinal axis. When placed about an ostium of a vessel associated with a chamber formed within a patient, the continuous lesion pattern established by the electrode electrically isolates the vessel from the chamber. For example, the catheter assembly may be provided for treatment of atrial fibrillation whereby the lesion pattern in formed to electrically isolate a pulmonary vein (vessel) from the left atrium (chamber). In one preferred embodiment, the catheter assembly further includes a mapping device for mapping tissue within the vessel.

Another aspect of the present invention relates to a catheter assembly for treatment of cardiac arrhythmia. The catheter assembly comprises a catheter body and at least one electrode. The catheter body includes a proximal portion, an intermediate portion and a distal portion. The intermediate portion extends from the proximal portion and defines a longitudinal axis. The distal portion extends from the intermediate portion and forms a substantially closed loop. The loop defines a loop axis substantially parallel to the longitudinal axis. The electrode is disposed along the loop. With this configuration, upon energization, the electrode ablates a continuous lesion pattern in a plane substantially perpendicular to the longitudinal axis. When placed in contact with tissue, the electrode ablates a continuous lesion pattern, isolating tissue within the lesion pattern. For example, the catheter assembly may be provided for treatment of atrial fibrillation whereby the lesion pattern is formed to electrically isolate a pulmonary vein from the left atrium. In one preferred embodiment, the catheter assembly further includes a mapping device extending distal the loop for mapping tissue.

Another aspect of the present invention relates to a method for forming an ablation pattern to electrically isolate a vessel, defining an ostium, from a chamber formed within a patient for treatment of cardiac arrhythmia. The method includes selecting a catheter assembly comprising a catheter body and at least one electrode. The catheter body defines a longitudinal axis and includes a proximal portion and a distal portion. The distal portion forms a substantially closed loop transverse to the longitudinal axis, the loop defining a loop axis substantially parallel to the longitudinal axis. The electrode is disposed along the loop. The distal portion of the catheter body is guided into the chamber and is directed to a position spaced from the vessel ostium, with the loop axis being substantially aligned with a center of the vessel ostium. The distal portion is advanced in a direction parallel with the loop axis such that the loop contacts the chamber wall about the vessel ostium. Finally, the electrode is energized to ablate a continuous lesion pattern about the vessel ostium to electrically isolate the vessel from the chamber. For example, the method may be utilized to electrically isolate a pulmonary vein (vessel) from the left atrium (chamber) by forming a lesion pattern about the pulmonary vein ostium. In one preferred embodiment, the method further includes mapping the vessel with a mapping electrode.

Yet another aspect of the present invention relates to a method of electrically isolating a vessel from a chamber formed within a patient, the vessel defining an ostium in a wall of the chamber, for treatment of cardiac arrhythmia. The method includes ablating a continuous, closed lesion pattern in the chamber wall about the vessel ostium. The lesion pattern electrically isolates the vessel from the chamber. For example, the method may be utilized to electrically isolate a pulmonary vein from the left atrium.

BRIEF DESCRIPTION OF THE DRAWINGS

FIG. 1A is a side-elevational view of a catheter assembly in accordance with the present invention;

FIG. 1B is a perspective view of a portion of the catheter assembly of FIG. 1A;

FIG. 1C is an end view of a portion of the catheter assembly of FIG. 1A;

FIG. 1D is an end view of a portion of an alternative catheter assembly in accordance with the present invention;

FIG. 4A is a side view of a portion of an alternative catheter assembly in accordance with the present invention;

FIG. 5A is a side view of a portion of an alternative catheter assembly in accordance with the present invention;

FIG. 6 is a side view of a portion of an alternative catheter assembly in accordance with the present invention;

FIG. 7 is a side view of a portion of an alternative catheter assembly in accordance with the present invention;

FIG. 10 is a side view of a portion of an alternative catheter assembly in accordance with the present invention;

FIG. 11 is a side view of a portion of an alternative catheter assembly in accordance with the present invention; and FIGS. 12A and 12B are side views of a portion of an alternative catheter assembly in accordance with the present invention.

DESCRIPTION OF THE PREFERRED EMBODIMENTS

Figure 2A:
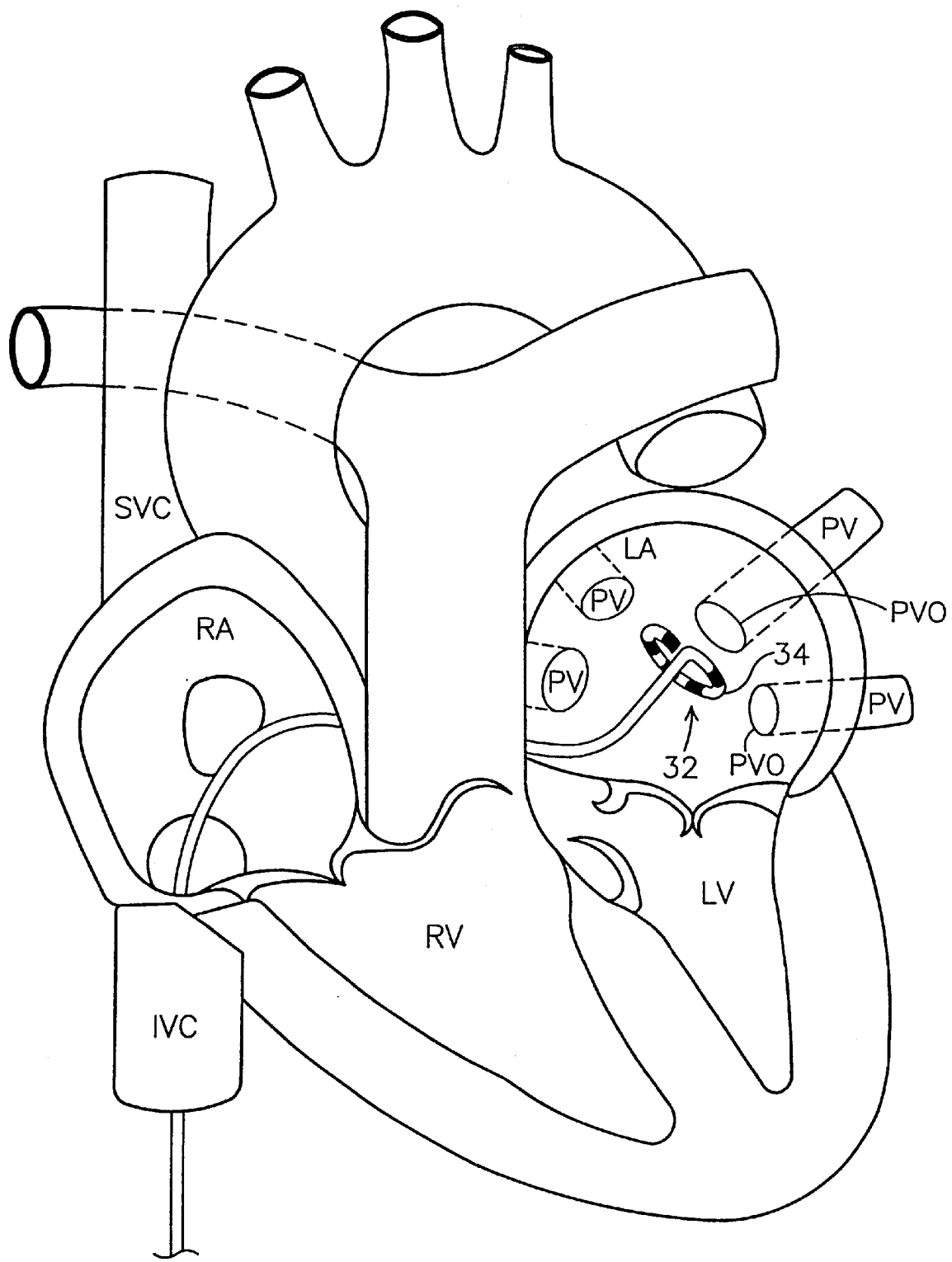
FIGS. 2A–2D illustrates use of the catheter assembly of FIG. 1A within a heart.

One preferred embodiment of a catheter assembly 20 in accordance with the present invention is shown in FIGS. 1A–1C. The catheter assembly 20 is comprised of a catheter body 22, a handle 24 and electrodes 26. As described in greater detail below, the catheter body 22 extends from the handle 24, and the electrodes 26 are disposed along a portion of the catheter body 22.

The catheter body 22 is defined by a proximal portion 28, an intermediate portion 30 and a distal portion 32, and includes a central lumen (not shown). Although not specifically shown, the catheter body may be configured for over-the-wire or rapid exchange applications. In one preferred embodiment, the proximal portion 28, the intermediate 30 and the distal portion 32 are integrally formed from a biocompatible material having requisite strength and flexibility for deployment within a heart. Appropriate materials are well known in the art and include polyamide.

The intermediate portion 30 extends from the proximal portion 28. The proximal portion 28 and the intermediate portion 30 are preferably flexible, so as to facilitate desired articulation during use. In general terms, however, the intermediate portion 30 defines a longitudinal axis L1. It should be recognized that in one position (shown in FIG. 1A), the longitudinal axis L1 extends linearly through the intermediate portion 30 and the proximal portion 28. Upon deployment, it may be that the proximal portion 28 and/or the intermediate portion 30 is forced to a curved or curvilinear orientation. With this in mind, the longitudinal axis L1 is more specifically defined as a center of the intermediate portion 30 adjacent a point of intersection between the distal portion 32 and the intermediate portion 30, as best shown in FIG. 1C.

The distal portion 32 extends from the intermediate portion 30 and forms a loop 34. In one preferred embodiment, the loop 34 is circular, formed in a plane transverse to the longitudinal axis L1. To this end, the distal portion 32 preferably includes a lateral segment 36. The lateral segment 36 extends in a generally lateral fashion from the intermediate portion 30. The loop 34 extends from the lateral segment 36 in an arcuate fashion, turning or revolving about a central loop axis C1 (shown best in FIG. 1B). While the loop 34 is shown in FIG. 1A as forming a single revolution about the central loop axis C1, the loop 34 may instead include a plurality of revolutions to define a spiral or coil. In the one preferred embodiment depicted in FIGS. 1A–1C, the central loop axis C1 is aligned with the longitudinal axis L1. Alternatively, however, the lateral segment 36 may be eliminated such that the loop 34 extends directly from the intermediate portion 30. Even further, the lateral segment 36 may be configured such that the central loop axis Cl is offset from the longitudinal axis L1. Regardless of the exact construction, however, the central loop axis C1 is preferably substantially parallel to the longitudinal axis L1.

As best shown in FIG. 1C, the loop 34 preferably extends to form a circle in a frontal plane. Alternatively, a variety of other shapes may also be useful. For example, as shown in FIG. 1D, a square-shaped loop is depicted. The loop 34 may further assume a triangular, rectangular, octagonal, or other closed shape. Returning to FIGS. 1A–1C, regardless of the exact shape, the loop 34 is preferably substantially closed and can be defined by a proximal end 40 and a distal end 42. To effectuate the preferred "closed" configuration of the loop 34, the distal end 42 is preferably adjacent the proximal end 40. In fact, the distal end 42 may contact the proximal end 40, although this relationship is not required. Alternatively, the distal end 42 may be longitudinally spaced from the proximal end 40. With this configuration, the distal portion 32 is preferably sufficiently flexible such that upon contact with a tissue wall, the distal end 42 will deflect proximally to a position adjacent the proximal end 40.

Regardless of the exact shape, the loop 34 preferably defines an enclosed area A greater than a size of an ostium (not shown) associated with a particular vessel to be isolated, as described in greater detail below. In one preferred embodiment, the catheter assembly 20 is configured to electrically isolate a pulmonary vein from the left atrium. With this one preferred application, where the loop 34 is circular, the loop 34 has a diameter in the range of approximately 10–20 mm, more preferably 15 mm, although other sizes, either greater or smaller, are acceptable.

The loop 34 may be formed in a variety of ways, such as by incorporating a preformed section of super elastic, shape memory material, such as Nitinol, with a loop configuration. To facilitate guiding of the distal portion 32 into a heart (not shown), the catheter assembly 20 may include a stylet (not shown) internally disposed within the catheter body 22. In an extended position, the stylet would extend through the distal portion 32, so as to render the loop 34 straight. Upon retraction of the stylet, the distal portion 32 would form the loop 34. Alternatively, the catheter assembly 20 may include a sheath (not shown) slidably receiving the catheter body 22. Prior to deployment, the distal portion 32 would be retracted within the sheath, rendering the loop 34 straight. Upon deployment from the sheath, the distal portion 32 would form the loop 34. Other similar approaches for providing the loop 34 are similarly acceptable.

The handle 24 is preferably sized to be grasped by a user and includes an electrical connector 44. The electrical connector provides electrical connections to the electrodes 26 carried by the distal portion 32. To this end, wire(s) (not shown) may extend within the central lumen (not shown) from the distal portion 32 to the handle 24.

The electrodes 26 are preferably of a type known in the art and are preferably a series of separate band electrodes spaced along the loop 34. Instead of, or in addition to, separate band electrodes, the electrodes 26 may include one or more spiral or coil electrodes, or one or more counterelectrodes. Additionally, the electrodes 26 are preferably non-thrombogenic, non-coagulum or char forming. The electrodes 26 may be cooled by a separate source (not shown), such as a saline source. The electrodes 26 may be electrically isolated from one another, or some or all of the electrodes 26 may be electrically connected to one another. Preferably, however, at least one electrode 26 is provided. The electrodes 26 are preferably shaped and positioned such that during an ablation procedure, a continuous, closed therapeutically-effective lesion pattern is created. Preferably, the length of each of the electrodes 26 is about 4–12 mm, more preferably about 7 mm. The spacing between each of the electrodes 26 is preferably about 1–3 mm, and more preferably about 2 mm. Finally, to effectuate a continuous, closed lesion pattern, preferably one of the electrodes 26 is disposed at the proximal end 40 of the loop 34, and another of the electrodes 26 is disposed at the distal end 42. As previously described, it is not necessary that the loop segment 38 be formed such that the proximal end 40 and the distal end 42 are integral. Instead, a slight spacing may exist. With this in mind, the spacing or gap between the electrode 26 at the proximal 40 and the electrode 26 at the distal end 42 is preferably less than about 5 mm.

Figure 2B:
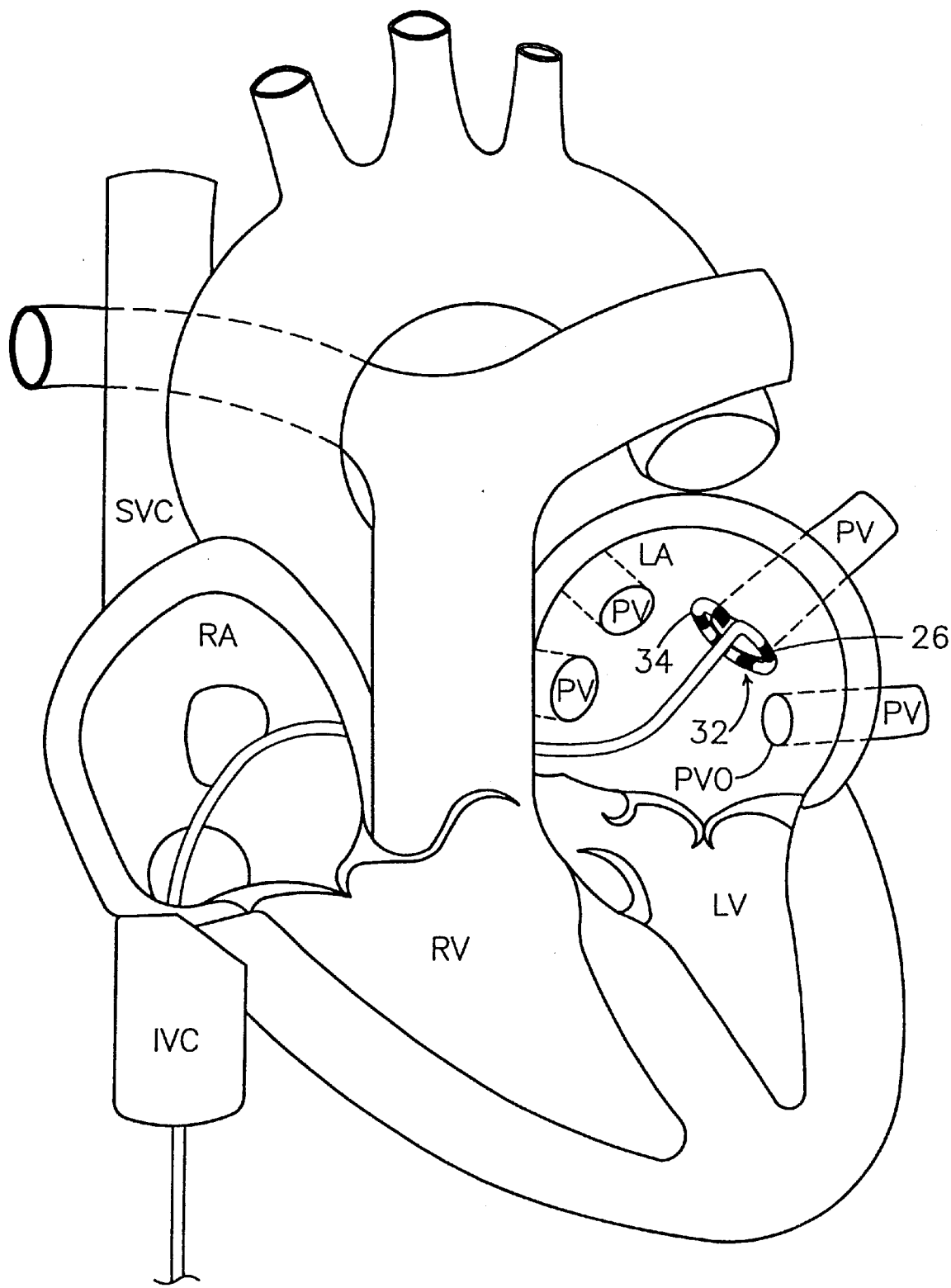

FIGS. 2A and 2B illustrate use of the catheter assembly 20 shown in FIGS. 1A–1C within a heart 50. As a point of reference, the heart 50 includes a right atrium RA, a left atrium LA, a right ventricle RV and a left ventricle LV. An inferior vena cava IVC and a superior vena cava SVC lead into the right atrium RA. The right atrium RA is separated from the left atrium LA by an interarterial septum (not shown). Finally, four pulmonary veins PV extend from the left atrium LA. Each of the pulmonary veins PV forms an ostium PVO in the left atrium LA wall. As previously described, during formation of the heart 50, it is possible that tissue of the left atrium LA may grow upwardly into one or more of the pulmonary veins PV. This left atrium LA tissue may spontaneously depolarize, resulting in atrial fibrillation. Notably, the heart 50 may be formed such that a separate ostium PVO is not formed for each individual pulmonary vein PV. In other words, a single pulmonary vein ostium PVO may be formed for two pulmonary veins PV. For example, a single pulmonary vein ostium PVO may be formed for both the left inferior pulmonary vein PV and the left superior pulmonary vein PV, with the two pulmonary veins PV bifurcating from the single ostium PVO.

As shown in FIG. 2A, electrical isolation of a pulmonary vein PV begins by directing the distal portion 32 of the catheter body 22 through the inferior vena cava IVC, into the right atrium RA through a puncture in the interarterial septum (not shown) and into the left atrium LA. Alternatively, the introduction of the distal portion 32 of the catheter body 22 into the right atrium RA is also suggested by passage of the distal portion 32 into the right atrium RA through the superior vena cava SVC. The loop 34 is positioned slightly spaced from the ostium PVO associated with the pulmonary vein PV to be treated. More particularly, the loop 34 is positioned such that the central loop axis C1 (FIG. 1B) is approximately aligned with a center of the pulmonary vein ostium PVO. The catheter body 22 is then advanced distally such that the loop 34 contacts the left atrium LA wall about the pulmonary vein ostium PVO in question, as shown in FIG. 2B. In other words, the catheter body 22 is advanced in a direction parallel with the central loop axis C1 such that the loop 34 contacts the left atrium LA wall, surrounding the pulmonary vein ostium PVO. Importantly, because the central loop axis C1 is parallel to the longitudinal axis L1, the catheter body 22 longitudinally supports advancement of the loop 34. In other words, the longitudinal axis L1 is effectively aligned with the pulmonary vein ostium PVO such that blood flow from the pulmonary vein PV acts along the longitudinal axis L1. Thus, the catheter body 22 limits deflection of the loop 34 otherwise caused by blood flow from the pulmonary vein PV.

Figure 2C:
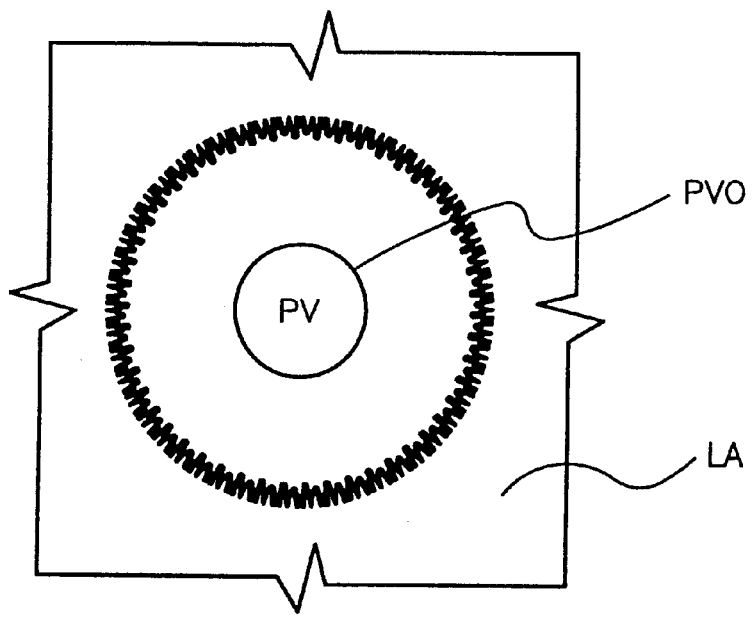
Figure 2D:
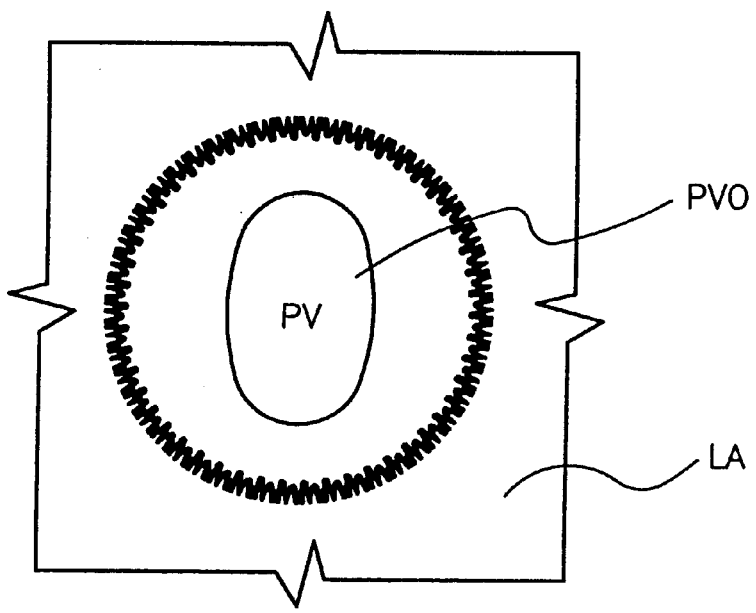

The electrodes 26 (shown best in FIGS. 1A–1C) are then energized to a sufficient level to ablate the contacted tissue, for example with an r.f. source. In one preferred embodiment, the electrodes 26 ablate the left atrium LA tissue for 30–120 seconds at a temperature in the range of approximately 60–70 degree C. As a result, a continuous, closed lesion pattern is formed around the pulmonary vein ostium PVO as shown in FIG. 2C. Pursuant to the above described catheter assembly 20 configuration, the lesion pattern is formed in a plane substantially perpendicular to the longitudinal axis L1. Notably, while the lesion pattern is shown as being only slightly larger than the pulmonary vein ostium PVO, the loop 34 (FIG. 1A) may be sized to produce an even larger ablation lesion pattern. To this end, where a single pulmonary vein ostium PVO is formed for two pulmonary veins PV, the resulting pulmonary vein ostium PVO may be elongated. As shown in FIG. 2D, then, the loop 34 (FIG. 1A) is configured to form a continuous, closed lesion pattern about the elongated-shaped pulmonary vein ostium PVO.

The continuous, closed lesion pattern electrically isolates the pulmonary vein PV from the left atrium LA. Any undesired electrical impulses generated in the pulmonary vein are effectively "stopped" at the lesion pattern, and will not propagate into the left atrium LA.

Figure 3C:
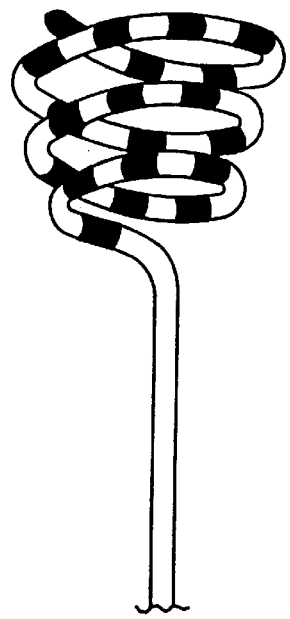
FIG. 3C is a side view of a portion of an alternative catheter assembly in accordance with the present invention.
Figure 3D:
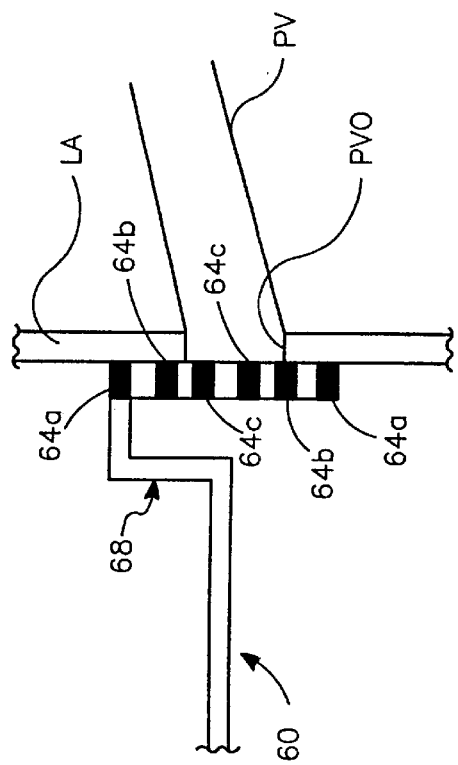
FIG. 3D is a simplified cross-sectional view of a portion of the heart and a portion of the catheter assembly of FIGS. 3A and 3B.
Figure 3A:
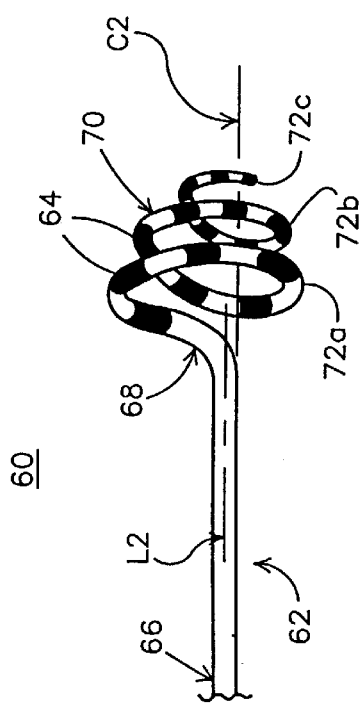
FIG. 3A is a side view of a portion of an alternative catheter assembly in accordance with the present invention.
Figure 3B:
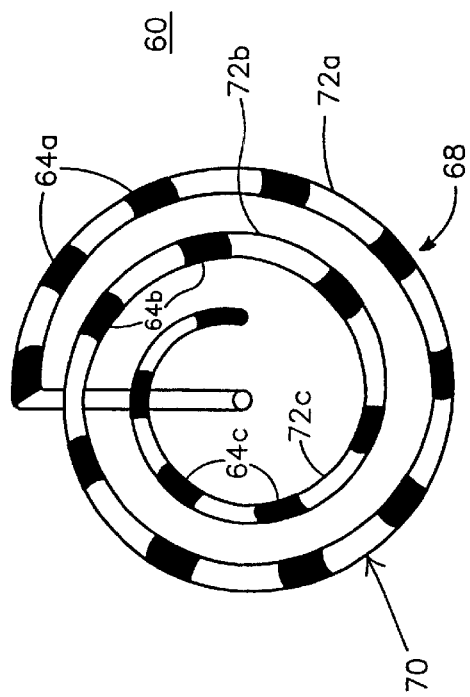
FIG. 3B is an end view of the catheter assembly of FIG. 3A.

An alternative catheter assembly 60 is shown in FIGS. 3A and 3B. The catheter assembly 60 includes a catheter body 62, a handle (not shown) and electrodes 64. The catheter body 62 includes a proximal portion (not shown), an intermediate portion 66 and a distal portion 68. For ease of illustration, the handle and the proximal portion of the catheter body 22 are not shown in FIGS. 3A and 3B, it being understood that these components are similar to the handle 24 and the proximal portion 28 shown in FIG. 1A. Similar to the catheter body 22, the intermediate portion 66 extends from the proximal portion and defines a longitudinal axis L2. The distal portion 68 extends from the intermediate portion 66 and forms a loop or coil 70 substantially transverse to the longitudinal axis L2 and includes a plurality of loop segments 72A–72C. The coil 70 is formed such that each of the loop segments 72A–72C revolves about a central loop axis C2. In one preferred embodiment, the central loop axis C2 is aligned with the longitudinal axis L2 defined by the intermediate portion 66. Alternatively, the central loop axis C2 may be offset from the longitudinal axis L2. Regardless, the central loop axis C2 is preferably substantially parallel with the longitudinal axis L2.

Each of the loop segments 72A–72C preferably defines a different diameter. For example, the first loop segment 72A defines a diameter slightly larger than that of the second loop segment 72B; whereas the second loop segment 72B defines a diameter slightly greater than that of the third loop segment 72C. In this regard, while each of the loop segments 72A–72C are depicted as being longitudinally spaced (such that the loop 70 forms a multi-lane spiral or coil), the loop segments 72A–72C may instead be formed in a single plane (such that the loop 70 forms a unitary plane spiral or coil). While the loop segments 72A–72C extend distal the intermediate portion 66 so as to define a descending or decreasing diameter, an opposite configuration may also be employed. For example, FIG. 3C depicts a coil 70' having loop segments distally increasing in diameter.

Returning to FIGS. 3A and 3B, the electrodes 64 are similar to the electrodes 26 (FIG. 1A) previously described, and preferably are band electrodes disposed along the loop segments 72A–72C. In this regard, each of the loop segments 72A–72C includes electrodes 64A–64C, respectively. In one preferred embodiment, a power source (not shown) associated with the electrodes 64 is configured to individually energize the electrodes 64 to varying levels. Further, the electrodes 64 are preferably configured to provide feedback information indicative of tissue contact, such as by including a thermocouple.

The catheter assembly 60 is used in a fashion highly similar to the method previously described for the catheter assembly 20 (as shown, for example, in FIGS. 2A–2C). Thus, for example, the distal portion 68 of the catheter body 62 is directed within the left atrium LA (FIG. 2A) such that the loop 70 is disposed about a pulmonary vein ostium PVO. It should be understood that one or more of the loop segments 72A–72C may define a diameter (or area) that is less than a diameter (or area) of the pulmonary vein ostium PVO in question. For example, in the simplified cross-sectional view of FIG. 3D, the electrodes 64C associated with the third loop segment 72C (FIG. 3A) are not in contact with the left atrium LA wall, but instead are within the area defined by the pulmonary vein ostium PVO. Conversely, the electrodes 64B associated with the second loop segment 72B (FIG. 3A) and the electrodes 64A associated with the first loop segment (FIG. 3A) are in contact with the left atrium LA wall. To avoid potential collateral damage caused by full energization of the electrodes 64C not in contact with the left atrium LA wall, each of the electrodes 64A–64C are selectively energized with a low energy supply. The energy level is not sufficient to ablate contacted tissue, but provides a low energy measurement, such as through a thermocouple or other sensing device associated with each of the electrodes 64A–64C. If the sensing device detects a temperature rise, an indication is given that the particular energized electrode 64A, 64B or 64C is in contact with tissue of the left atrium LA. Following the low energy measurement procedure, only those electrodes determined to be in contact with the left atrium LA (for example, electrodes 64A and 64B) are powered to ablate a continuous, closed lesion pattern about the pulmonary vein ostium PVO, as previously described.

Another alternative embodiment of a catheter assembly 80 is shown in FIG. 4A. The catheter assembly 80 includes a catheter body 82, an electrode 84 and a locating device 86. For ease of illustration, only a portion of the catheter assembly 80 is shown, and catheter assembly 80 may further include a handle similar to the handle 24 associated with the catheter assembly 20 (FIG. 1A) previously described.

Catheter body 82 is defined by a proximal portion (not shown), an intermediate portion 88 and a distal portion 90. The intermediate portion 88 extends from the proximal portion and is defined by a proximal segment 92 and a distal segment 94. In a preferred embodiment, the distal segment 94 is preferably more flexible than the proximal segment 92. With this configuration, the distal segment 94 can more easily deflect relative to the proximal segment 92, thereby facilitating desired positioning of the distal portion 90 during deployment. In this regard, an internal pull wire (not shown) may be provided to effectuate desired deflection of the distal segment 94. Even further, an anchor 96 is preferably included for facilitating a more radical displacement of the distal portion 90 relative to the intermediate portion 88.

As with previous embodiments, the intermediate portion 88 defines a longitudinal axis L3. Once again, where the intermediate portion 88 is axially aligned with the proximal portion (not shown), the longitudinal axis L3 is linear along the intermediate portion 88 and the proximal portion. However, because the intermediate portion 88 is preferably bendable relative to the proximal portion, and further because the distal segment 94 may bend relative to the proximal segment 92, the longitudinal axis L3 is more succinctly defined by the intermediate portion 88 at the point of intersection between the intermediate portion 88 and the distal portion 90.

Similar to the catheter assembly 20 (FIG. 1A) previously described, the distal portion 90 preferably forms a loop 98. The loop 98 may include one or more loop segments (one is shown in FIG. 4A), with each loop segment revolving around a central loop axis C3. The loop 98 is formed substantially transverse to the longitudinal axis L3, with the central loop axis C3 preferably aligned with the longitudinal axis L3. Alternatively, the central loop axis C3 may be slightly offset from the longitudinal axis L3. Regardless, the central loop axis C3 is preferably parallel with the longitudinal axis L3.

The electrode 84 is shown in FIG. 4 as being a continuous coil electrode. Alternatively, a plurality of spaced, band electrodes or counter-electrodes may be used.

Finally, the locating device 86 includes a tip 100 configured to extend distal the loop 98. In one preferred embodiment, the locating device 86 is integrally formed with the catheter body 82, extending from the distal portion 90. Alternatively, the locating device 86 may be a separate body. Regardless, the tip 100 extends distal the distal portion 90, and is aligned with the central loop axis C3 defined by the loop 98. The tip 100 preferably has a diameter less than a diameter of a pulmonary vein, and a length in the range of approximately 1–15 mm. Further, as shown in FIG. 4, the tip 100 may include a series of mapping electrodes 102. The mapping electrodes 102 are electrically connected to an external recording system (not shown) for providing information indicative of tissue polarization.

Figure 4B:
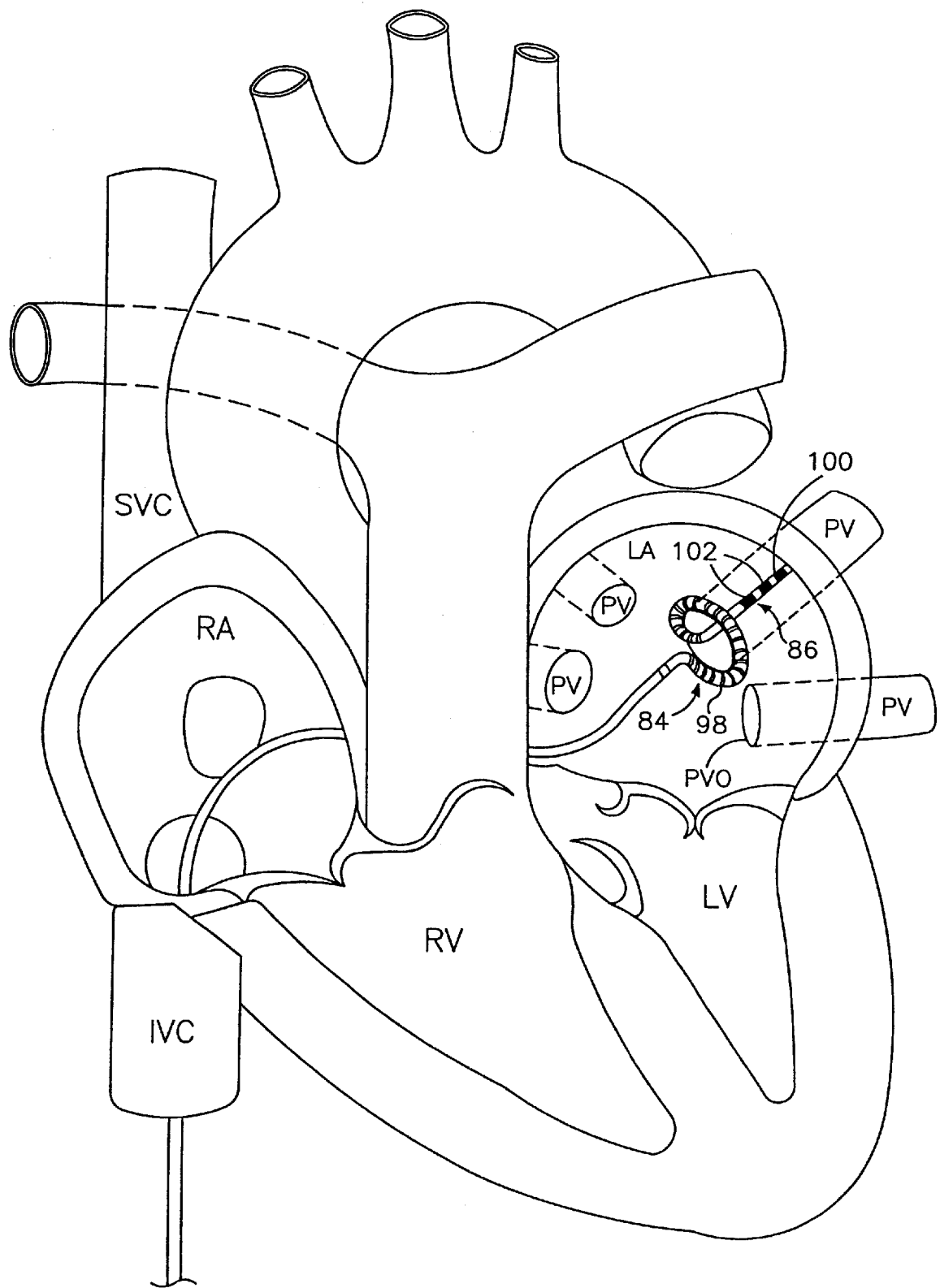
FIG. 4B illustrates placement of the catheter assembly of FIG. 4A within the left atrium of a heart.

As shown in FIG. 4B, during use, the catheter assembly 80 is directed into the left atrium LA as previously described. The locating device 86, and in particular the tip 100, is then used to locate the pulmonary vein ostium PVO. Once located, the tip 100 is inserted into the pulmonary vein PV, effectively centering the loop 98 around the pulmonary vein ostium PVO. Where the tip 100 includes the mapping electrodes 102, a mapping procedure can be performed, whereby information indicative of tissue activity nearby the mapping electrodes 102 is provided. During this mapping procedure, a determination can be made as to whether the particular pulmonary vein PV is generating undesired electrical impulses. Where it is determined that, in fact, tissue in the pulmonary vein PV is spontaneously depolarizing, the electrode 84 is energized to form the continuous, closed lesion pattern about the pulmonary vein ostium PVO as previously described.

Yet another alternative embodiment of a catheter assembly 110 in accordance with the present invention is shown in FIG. 5. The catheter assembly 110 is highly similar to the catheter assembly 80 (FIG. 4A) and includes a catheter body 112, electrodes 114 and a locating device 116. The catheter body 112 includes a proximal portion (not shown) an intermediate portion 88 defining a longitudinal axis L4 and a distal portion 120. The distal portion 120 extends from the intermediate portion 118 and forms a loop 122 substantially transverse to the longitudinal axis L4. In this regard, the loop 122 revolves about a central loop axis C4. In one preferred embodiment, the central loop axis C4 is aligned with the longitudinal axis L4. Alternatively, the central loop axis C4 is offset from, but substantially parallel with, the longitudinal axis L4. The electrodes 114 (shown as spaced band electrodes) are disposed along the loop 122 for forming a continues, closed lesion pattern.

The locating device 116 includes a tip 124 that extends distal the loop 122. In one preferred embodiment, the locating device 116 is integrally formed with the catheter body 112 and includes mapping electrodes 126 connected to an external recording device (not shown). Alternatively, the locating device 116 may be a separate body. As shown in FIG. 5, the tip 124 forms a descending diameter coil, generally aligned with the central loop axis C4. By providing a coil configuration for the tip 124, the tip 124 facilitates a more positive centering of the loop 122 about a pulmonary vein ostium PVO (FIG. 4B). In one preferred embodiment, the tip 124 defines a maximum diameter approximating a diameter of a pulmonary vein. When inserted within a pulmonary vein, then, the tip 124 effectively lodges along the pulmonary vein wall. This, in turn, positions the loop 122 in a more central fashion about the associated ostium. Further, by providing the mapping electrodes 126, the locating device 116 additionally serves as a mapping device for evaluating a particular pulmonary vein.

It should be recognized that other devices can be provided to assist in centering the ablation loop about the pulmonary vein ostium. For example, yet another alternative embodiment of a catheter assembly 130 is depicted in FIG. 6. The catheter assembly includes a catheter body 132, electrodes 134, a balloon 136 and a locating device 138. The catheter body 132 is similar to those previously described, and includes a proximal portion (not shown) an intermediate portion 140 defining a longitudinal axis L5 and a distal portion 142. The distal portion 142 extends from the intermediate portion 140 and forms a loop 144 substantially transverse to the longitudinal axis L5. The loop 144 revolves about a central loop axis C5, that, in one preferred embodiment, is aligned with the longitudinal axis L5. The balloon 136 is disposed along the distal portion 142 distal the loop 144. In one preferred embodiment, the balloon 136 is fluidly connected to a fluid source (not shown), such as a pressurized reservoir of saline, by a lumen (not shown) formed within the catheter body 132. Finally, the locating device 138 includes a tip 146 extending distal the loop 144. In one preferred embodiment, as shown in FIG. 6, the locating device 138 is integrally formed with the catheter body 132, with the tip 146 extending distal the balloon 136. Alternatively, the locating device 138 may be a separate body, and the tip 146 may be positioned between the loop 144 and the balloon 136. Regardless, the tip 146 preferably includes mapping electrodes 148.

During use, the locating device 138 is used to locate a pulmonary vein PV (FIG. 4B) via the tip 146. The tip 146 axially inserted into the pulmonary vein PV. The mapping electrodes 148 may then be used to ascertain whether tissue in the pulmonary vein PV is spontaneously generating unexpected electrical impulses. Upon determining that the pulmonary vein PV requires electrical isolation, the catheter body 132 is deployed such that the loop 144 contacts the left atrium LA (FIG. 4B) wall (as previously described). The balloon 136 is inflated such that it engages the pulmonary vein PV wall. Once inflated, the balloon 136 positively centers the loop 144 about the pulmonary vein ostium PVO (FIG. 4B).

Yet another alternative embodiment of a catheter assembly 160 is shown in FIG. 7. The catheter assembly 160 includes a catheter body 162, electrodes 164, a wire basket 166 and a locating device 168. As with previous embodiments, the catheter body 162 includes a proximal portion (not shown), an intermediate portion 170 defining a longitudinal axis L6 and a distal portion 172. The distal portion 172 extends from the intermediate portion 170 and forms a loop 174 transverse to the longitudinal axis L6. In this regard, the loop 174 revolves around a central loop axis C6 that, in one preferred embodiment, is aligned with the longitudinal axis L6.

The wire basket 166 is maintained by the distal portion 172 distal the loop 174. The wire basket 166 may be radially extended and retracted via a pull wire or similar activation device extending through a lumen (not shown) formed within the catheter body 162.

Finally, the locating device 168 includes a tip 176 positioned distal the loop 174. In one preferred embodiment, the locating device 168 is integrally formed with the catheter body 162 and includes mapping electrodes 178. Alternatively, the locating device 168 may be a separate body, and the tip 176 may be disposed between the wire basket 166 and the loop 174.

During use, the catheter assembly 160 functions in a fashion highly similar to the catheter assembly 130 (FIG. 6) previously described. The locating device 168, and in particular the tip 176, is used to locate and map a pulmonary vein PV (FIG. 4B). The loop 174 is maneuvered into contact with the left atrium LA (FIG. 4B) wall. The wire basket 166 is then radially deployed so as to engage the pulmonary vein PV wall. In this deployed position, the wire basket 166 serves to positively center the loop 174 about the pulmonary vein ostium PVO (FIG. 4B).

Figure 8:
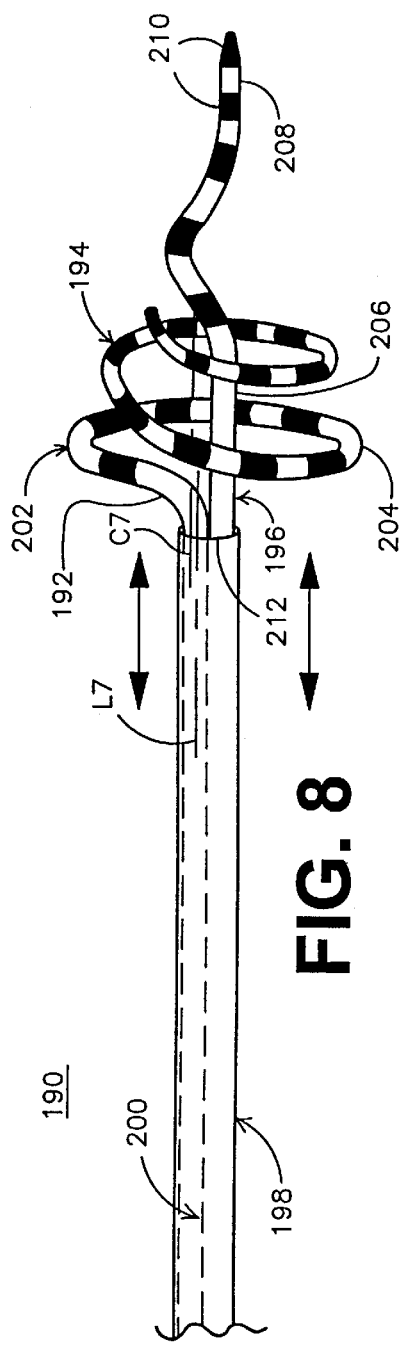
FIG. 8 is a side view of a portion of an alternative catheter assembly in accordance with the present invention.

Yet another alternative embodiment of a catheter assembly 190 is shown in FIG. 8. The catheter assembly 190 includes a catheter body 192 (shown partially in FIG. 8), electrodes 194, a locating device 196 and a guide catheter or sheath 198. As described in greater detail below, the sheath 198 coaxially maintains the catheter body 192 and the locating device 196 such that each of the catheter body 192 and the locating device 196 are slidable between a retracted position and a deployed position (shown in FIG. 8).

The catheter body 192 is virtually identical to the catheter body 62 (FIG. 3A) previously described and includes a proximal portion (not shown), an intermediate portion 200 defining a longitudinal axis L7 and a distal portion 202. The distal portion 202 extends from the intermediate portion 200 and forms a coil or plurality of loops 204 substantially transverse to the longitudinal axis L7. Alternatively, the coil 204 may form a single loop. The coil 204 revolves around a central loop axis C7, that, in one preferred embodiment, is aligned with the longitudinal axis L7. The distal portion 202, and in particular the coil 204, is preferably sufficiently flexible so as to assume a relatively straight configuration when retracted within the sheath 198. Further, the distal portion 202 includes a shape memory characteristic such that when deployed from the sheath 198, the distal portion 202 forms the coil 204 as shown in FIG. 8.

The electrodes 194 are identical to those previously described and preferably comprise band electrodes disposed along the coil 204. Alternatively, a continuous coil electrode or counter-electrode may be provided.

The locating device 196 is relatively rigid and includes a shaft 206 defining a tip 208 that preferably maintains mapping electrodes 210. The shaft 206 is sized to be slidably received within a lumen (not shown) in the sheath 198. As shown in FIG. 8, the tip 208 preferably assumes a coil shape with decreasing diameter. Alternatively, the tip 208 may be substantially straight. Preferably, however, the tip 208 is sufficiently flexible such that upon retraction into the sheath 198, the tip 208 assumes a relatively straight form. Additionally, the tip 208 has a shape memory characteristic such that upon deployment from the sheath 198, the tip 208 assumes the coiled shape shown in FIG. 8. For example, the tip 208 may include stainless steel or Nitinol core wires. Further, the tip 208 may be formed from a shape memory alloy of Nitinol that forms the coil shape when heated above a certain temperature. The heat may be achieved through resistive heating of the wire directly, or by surrounding the wire with a tubular heater.

The sheath 198 includes a proximal end (not shown) and a distal end 212, and forms at least one central lumen (not shown) sized to maintain the catheter body 192 and the locating device 196. Alternatively, a separate lumen may be provided for each of the catheter body 192 and the locating device 196. Regardless, the sheath 198 is configured to slidably maintain each of the catheter body 192 and the locating device 196 in a relatively close relationship. In one preferred embodiment, the sheath 198 is formed of a relatively soft material such as 35D or 40D Pebex.

As described above, each of the catheter body 192 and the locating device 196 are slidable relative to the sheath 198. In a deployed position (depicted in FIG. 8), the distal portion 202 of the catheter body 192 and the tip 208 of the locating device 196 extend distally from the sheath 198. More particularly, the locating device 196 is positioned such that the tip 208 is distal the coil 204. In this extended position, the tip 208 is essentially aligned with the central loop axis L7.

During use, the catheter body 192 and the locating device 196 are retracted within the sheath 198. The sheath 198 is then guided to the left atrium LA (FIG. 4B). The catheter body 192 and the locating device 196 are deployed from the sheath 198. More particularly, the distal portion 202 of the catheter body 192 and the tip 208 of the locating device 196 are extended from the distal end 212 of the sheath 198 (as shown in FIG. 8). A locking device (not shown) is preferably provided to secure the catheter assembly 190 in the deployed position. As previously described, upon deployment, the distal portion 202 forms the coil 204, whereas the tip 208 preferably assumes a coil shape. The tip 208 locates and is directed axially into a pulmonary vein PV as previously described. The mapping electrodes 210 sample electrical activity of the pulmonary vein tissue. If the mapping procedure determines that the pulmonary vein PV requires electrical isolation, the sheath 198 is guided in a direction along the central loop axis C7 until the coil 204 contacts the left atrium LA (FIG. 4B) wall about the pulmonary vein ostium PVO (FIG. 4B). Because the catheter body 192 and the locating device 196 are directly connected by the sheath 198, the tip 208 effectively positively centers the loop 204 about the pulmonary vein ostium PVO. The electrodes 194 may be selectively energized with a low energy supply to determine which of the electrodes 194 are in contact with tissue of the left atrium LA. Some or all of the electrodes 194 are then energized to ablate a continuous, closed lesion pattern about the pulmonary vein ostium PVO, thereby electrically isolating the pulmonary vein PV from the left atrium LA.

While the catheter assembly 190 has been described as including the sheath 198 to maintain the catheter body 192 and the locating device 196, the sheath 198 may be eliminated for example, the catheter body 192 may alternatively be configured to include lumen (not shown) sized to slidably receive the locating device 192. In this regard, the locating device 192 may serve as a guide wire, with the catheter body 192 riding over the locating device 192 much like an over-the-wire catheter configuration commonly known in the art. Even further, the catheter body 192 may include a rapid exchange design characteristic for quick mounting to removal from the locating device 190.

Figure 9A:
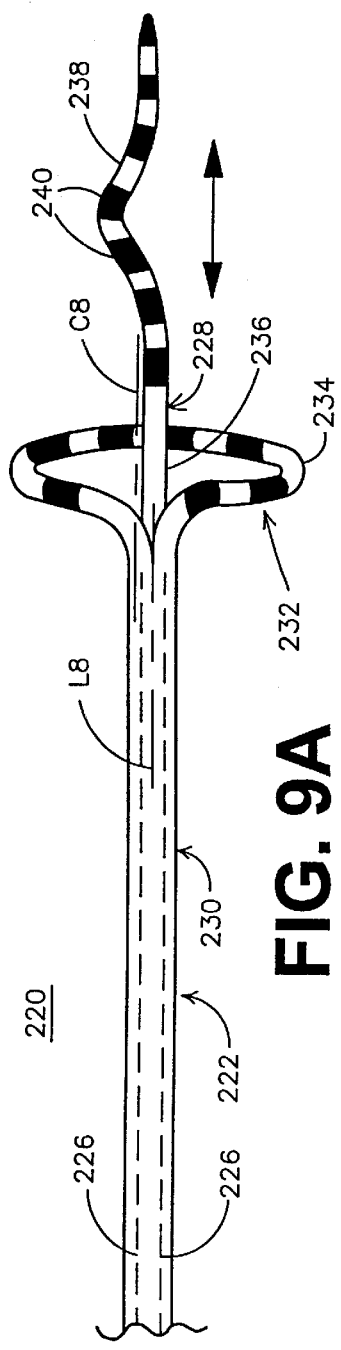
FIG. 9A is a side view of a portion of an alternative catheter assembly in accordance with the present invention, in a deployed position.
Figure 9B:
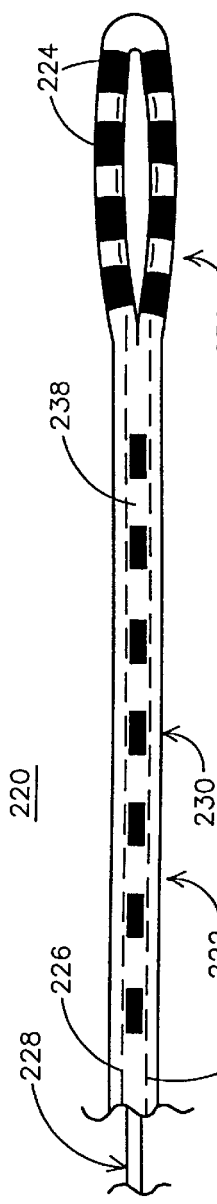
FIG. 9B is a side view of the catheter assembly of FIG. 9A in a retracted position.

Yet another alternative embodiment of a catheter assembly 220 is shown in FIGS. 9A and 9B. The catheter assembly 220 includes a catheter body 222 (shown partially in FIGS. 9A and 9B), electrodes 224, stylets 226 and a locating device 228. The electrodes 224 are disposed along a portion of the catheter body 222. The stylets 226 are slidably maintained within the catheter body 222. Finally, the locating device 228 is slidably maintained by the catheter body 222.

The catheter body 222 is similar to those previously described and includes a proximal portion (not shown), an intermediate portion 230, defining a longitudinal axis L8, and a distal portion 232. The distal portion 232 forms a loop 234 substantially transverse to the longitudinal axis L8. The loop 234 revolves around a central loop axis C8 which, in one preferred embodiment, is aligned with the longitudinal axis L8. The distal portion 232 is preferably sufficiently flexible so as to be relatively straight in a retracted position (FIG. 9B). Further, the distal portion 232 has a shape memory characteristic such that the distal portion 232 forms the loop 234 in a deployed position (FIG. 9A). For example, the catheter body 222 may be formed of a super elastic, shape memory Nitinol alloy.

Each of the stylets 226 are relatively rigid shafts sized to be slidably received within lumens (not shown) formed by the catheter body 222. To this end, as shown in FIG. 9A, in a deployed position, the stylets 226 are proximal the distal portion 232 such that the distal portion 232 is allowed to form the loop 234. Conversely, in a retracted position (FIG. 9B) the stylets 226 extend into the distal portion 232, thereby rendering the distal portion 232 substantially straight.

The electrodes 224 are identical to those previously described and preferably comprise band electrodes disposed along the loop 234. Alternatively, a continuous coil electrode or counter electrode may be provided.

The locating device 228 includes a shaft 236 having a tip 238. Similar to previous embodiments, the tip 238 is preferably coil shaped, and includes mapping electrodes 240. In this regard, the tip 238 is preferably sufficiently flexible such that in the retracted position (FIG. 9B), the tip 238 is rendered relatively straight by the catheter body 222. Conversely, in the deployed position (FIG. 9A), the tip 238 assumes the coiled shape. Alternatively, the tip 238 may be substantially straight in the deployed position.

The catheter assembly 220 is used in a manner highly similar to that previously described. The catheter assembly 220 is initially placed in the retracted position (FIG. 9B), whereby the stylets 226 are maneuvered distally to straighten the distal portion 232. Further, the locating device 228 is retracted within the catheter body 222 such that tip 238 is proximal the distal portion 232 and is rendered relatively straight. In this retracted position, the catheter assembly 222 can more easily be directed into the left atrium LA (FIG. 4B) as previously described. Once in the left atrium LA, the catheter assembly 220 is maneuvered to the deployed position (FIG. 9A), whereby the stylets are moved proximally such that the distal portion 232 forms the loop 234. Further, the locating device 228 is maneuvered distally relative to the catheter body 222 such that the tip 238 extends distal the loop 234. In the deployed position, the locating device 228 is maneuvered in a generally axial fashion to locate and extend into a pulmonary vein PV. The mapping electrodes 240 map the pulmonary vein tissue (FIG. 4B). Where the mapping procedure indicates that the pulmonary vein PV requires electrical isolation, the catheter assembly 220 is advanced such that the loop 234 surrounds the pulmonary vein ostium PVO (FIG. 4B). More particularly, the catheter assembly 220 is advanced in the direction of the central loop axis C8. Once again, the unique configuration of the catheter assembly 220 facilitates movement in an axial direction (relative to the pulmonary vein ostium PVO) as opposed to a radial, sliding direction required by previous ablation catheter designs. Notably, because the locating device 228 is directly connected to the catheter body 222, the locating device 228 facilitates positive centering of the loop 234 about the pulmonary vein ostium PVO. The electrodes 224 are then energized to ablate a continuous, closed lesion pattern about the pulmonary vein ostium PVO, thereby electrically isolating the pulmonary vein PV.

Yet another alternative embodiment of the catheter assembly 250 in accordance with the present invention is shown in FIG. 10. The catheter assembly 250 includes a catheter body 252 (shown partially in FIG. 10), electrodes 254, a locating device 256 and a guide catheter or sheath 258. As described in greater detail below, the sheath 258 coaxially maintains the catheter body 252 and the locating device 256 such that each of the catheter body 252 and the locating device 256 are slidable between a retracted position and a deployed position (shown in FIG. 10).

The catheter body 252 is virtually identical to the catheter body 62 (FIG. 3A) previously described and includes a proximal portion (not shown), an intermediate portion 260 defining a longitudinal axis L9 and a distal portion 262. The distal portion 262 extends from the intermediate portion 260 and forms a coil or loops 264 substantially transverse to the longitudinal axis L9. Alternatively, the coil 264 may form a single loop. The coil 264 revolves around a central loop axis C9, that, in one preferred embodiment, is aligned with the longitudinal axis L9. The distal portion 262, and in particular the coil 264, is preferably sufficiently flexible so as to assume a relatively straight configuration when retracted within the sheath 258. Further, the distal portion 262 includes a shape memory characteristic such that when deployed from the sheath 258, the distal portion 262 forms the coil 264 as shown in FIG. 10.

The electrodes 254 are identical to those previously described and preferably comprise band electrodes disposed along the coil 264. Alternatively, a continuous coil electrode or counter-electrode may be provided.

The locating device 256 includes a shaft 266 and a balloon 268. The shaft 266 includes a distal portion 270 and a tip 272. The distal portion 270 preferably forms an expansion joint 274. The tip 272 is distal the expansion joint 274 and preferably maintains mapping electrodes 276. The balloon 268 is sealed to the distal portion 270 of the shaft 266 about the expansion joint 274. In this regard, the expansion joint 274 is configured to be manipulated between a contracted position (FIG. 10) and an expanded position. In the expanded position, the expansion joint 274 extends axially so as to collapse the balloon 268. When collapsed, the balloon 268 can more easily be retracted within the sheath 258.

The sheath 258 includes a proximal end (not shown) and a distal end 278, and forms at least one central lumen (not shown) sized to maintain the catheter body 252 and the locating device 256. Alternatively, a separate lumen may be provided for each of the catheter body 252 and the locating device 256. Regardless, the sheath 258 is configured to slidably maintain each of the catheter body 252 and the locating device 256 in relatively close relationship. In one preferred embodiment, the sheath 258 is formed of a relatively soft material such as 35D or 40D Pebex.

As described above, each of the catheter body 252 and the locating device 256 are slidable relative to the sheath 258. In a deployed position (depicted in FIG. 10), the distal portion 262 of the catheter body 252 and the distal portion 270 of the locating device 256 extend distally from the sheath 258. More particularly, the coil 264 is positioned distal the distal end 278 of the sheath 258. Further, the distal portion 270, including the balloon 268, of the locating device 256 is positioned distal the coil 264. In this position, the distal portion 270 is essentially aligned with the central loop axis L9.

Prior to use, the catheter body 252 and the locating device 256 are retracted within the sheath 258. The sheath 258 is then guided to the left atrium LA (FIG. 4B). The catheter body 252 and the locating device 256 are deployed from the sheath 258. More particularly, the distal portion 262 of the catheter body 252 and the distal portion 270 of the locating device 256 are extended from the distal end 278 of the sheath 258 (as shown in FIG. 10). A locking device (not shown) is preferably provided to secure the catheter assembly 250 in the deployed position. As previously described, upon deployment, the distal portion 262 of the catheter body 252 forms the coil 264. The distal portion 270 of the locating device 256, including the balloon 268, is positioned distal the coil 264. The tip 272 locates and is directed axially into a pulmonary vein PV (FIG. 4B) as previously described. The mapping electrodes 276 sample electrical activity of the pulmonary vein tissue. If the mapping procedure determines that the pulmonary vein PV requires electrical isolation, the sheath 258 is guided in a direction along the central loop axis C9 until the coil 264 contacts the left atrium LA wall about the pulmonary vein ostium PVO (FIG. 4B). The expansion joint 274 is contracted and the balloon 268 inflated. Once inflated, the balloon 268 engages the pulmonary vein PV. Because the catheter body 252 and the locating device 256 are directly connected by the sheath 258, the balloon 268 effectively positively centers the coil 264 about the pulmonary vein ostium PVO. The electrodes 254 may be selectively energized with a low-energy supply to determine which of the electrodes 254 are in contact with the tissue of the left atrium LA. Some or all of the electrodes 254 are then energized to ablate a continuous, closed lesion pattern about the pulmonary vein ostium PVO, thereby electrically isolating the pulmonary vein PV from the left atrium LA.

Yet another alternative embodiment of a catheter assembly 290 is shown in FIG. 11. The catheter assembly 290 is highly similar to the catheter assembly 250 (FIG. 10) previously described, and includes a catheter body 292, electrodes 294, a locating device 296 and a guide catheter or sheath 298. The sheath 298 coaxially maintains the catheter body 292 and the locating device 296 such that each of the catheter body 292 and the locating device 296 are slidable between a retracted position and a deployed position (shown in FIG. 11).

The catheter body 292 includes a proximal portion (not shown), an intermediate portion 300 defining a longitudinal axis L10 and a distal portion 302. The distal portion 302 extends from the intermediate portion 300 and forms a coil or plurality of loops 304 substantially transverse to the longitudinal axis L10. Alternatively, the coil 304 may form a single loop. The coil 304 revolves around a central loop axis C10, that, in one preferred embodiment, is aligned with the longitudinal axis L10. The distal portion 302, and in particular the coil 304, is preferably sufficiently flexible so as to assume a relatively straight configuration when retracted within the sheath 298. Further, the distal portion 302 includes a shape memory characteristic such that when deployed from the sheath 298, the distal portion 302 forms the coil 304 as shown in FIG. 11.

The electrodes 294 are identical to those previously described and preferably comprise band electrodes disposed along the coil 304. Alternatively, a continuous coil electrode or counter-electrode may be provided.

The locating device 296 includes a shaft 306 and a wire basket 308. The shaft 306 includes a distal portion 310 and a tip 312. The distal portion 310 forms an expansion joint 314. The tip 312 preferably maintains mapping electrodes 316. The wire basket 308 is secured to the distal portion 310 about the expansion joint 314. With this configuration, the expansion joint 314 can be manipulated between an expanded position in which the wire basket 308 is relatively flat and a contracted position (FIG. 11) in which the wire basket 308 expands radially.

The sheath 298 is highly similar to previous embodiments and includes a proximal end (not shown) and a distal end 318, and forms at least one central lumen (not shown) sized to maintain the catheter body 292 and the locating device 296. Alternatively, a separate lumen may be provided for each of the catheter body 292 and the locating device 296. Regardless, the sheath 298 is configured to slidably maintain each of the catheter body 292 and the locating device 296 in a relatively close relationship.

As described above, each of the catheter body 292 and the locating device 296 are slidable relative to the sheath 298. In a deployed position (depicted in FIG. 11), the distal portion 302 of the catheter body 292 and the distal portion 310 of the locating device 296 extend distally from the sheath 298. More particularly, the catheter body 292 is positioned such that the coil 304 is distal the distal end 318. Further, the distal portion 310 of the locating device 296 is distal the coil 304.

During use, the catheter assembly 290 functions in a manner highly similar to the catheter assembly 250 (FIG. 10) previously described. However, the wire basket 308 is used to positively center the coil 304 about a pulmonary vein ostium PVO instead of the balloon 268 (FIG. 10) previously described.

Yet another alternative embodiment of the catheter assembly 330 is shown in FIGS. 12A and 12B. The catheter assembly 330 includes a catheter body 332 (shown partially in FIGS. 12A and 12B), a wire basket 334, a locating device 336 and a stylet or guide wire 338. The wire basket 334 is secured to the catheter body 332. The locating device 336 is preferably integrally formed with the catheter body 332 and includes a balloon 340. Finally, the guide wire 338 is slidably disposed within a central lumen (not shown) in the catheter body 332 and the locating device 336.

The catheter body 332 includes a proximal portion (not shown), an intermediate 342 defining a longitudinal axis L11 and a distal portion 344. The distal portion 344 maintains a proximal collar 346 and a distal collar 348. In a preferred embodiment, the proximal collar 346 is slidable relative to the distal collar 348.

The wire basket 334 is secured to the distal portion 344 by the proximal collar 346 and the distal collar 348. Further, the wire basket 334 includes a plurality of individual wire struts 350 each maintaining an electrode 352. In a preferred embodiment, the wire struts 350 are preferably tubular and are fluidly connected to a cooling source. The electrodes 352 are preferably disposed along the wire struts 350, respectively, slightly distal of a central position. With this configuration, the wire basket 334 can be maneuvered between a retracted position (FIG. 12A) and an expanded position (FIG. 12B) with movement of the proximal collar 346 relative to the distal collar 348. Notably, in the expanded position of FIG. 12B, the wire basket 334 positions the electrodes 352 so as to form a loop transverse to the longitudinal axis L11. More particularly, the loop formed in the expanded position revolves around a central loop axis C11, that, in one preferred embodiment, is aligned with the longitudinal axis L11.

The electrodes 352 are identical to those previously described and preferably comprise band electrodes disposed along the wire basket 334.

The locating device 336 extends distal the distal collar 348, and maintains the balloon 340 and mapping electrodes 354. The balloon 340 is fluidly connected to an inflation source (not shown) by a lumen (not shown) formed within the catheter body 332. As shown in FIGS. 12A and 12B, the balloon 340 is preferably positioned distal the wire basket 334. Further, the mapping electrode 354 is positioned distal the balloon 340.

Prior to use, the catheter assembly 330 is positioned in the retracted position shown in FIG. 12A. The guide wire 338 is guided to the left atrium LA (FIG. 4B) and into a pulmonary vein PV (FIG. 4B). The catheter body 332, including the locating device 336, are guided over the guide wire 338 to a point adjacent the pulmonary vein. The catheter body 332 is then advanced such that the locating device 336 enters the pulmonary vein PV. The mapping electrodes 354 sample electrical activity of the pulmonary vein tissue. If the mapping procedure determines that the pulmonary vein PV requires electrical isolation, the catheter assembly 330 is maneuvered to the expanded position shown in FIG. 12B, whereby the wire basket 334 expands radially. The catheter body 332 is then advanced axially toward the pulmonary vein such that the wire basket 334 contacts the left atrium LA about the pulmonary vein ostium PVO (FIG. 4B). The balloon 340 is then inflated so as to engage the pulmonary vein PV. Once inflated, the balloon 340 effectively centers the wire basket 334, and thus the electrodes 352, about the pulmonary vein ostium PVO. The electrodes 352 are then energized to ablate a continuous, closed lesion pattern about the pulmonary vein ostium PVO, thereby electrically isolating the pulmonary vein PV from the left atrium LA. If necessary, the individual wire struts 350 are cooled, such as by forcing a cooling liquid through the wire struts 350. The balloon 340 is deflated and the wire basket 334 maneuvered to the contracted position (FIG. 12A). The entire catheter assembly 330 may then be removed from the patient. Alternatively, the catheter body 332 may be retracted from the patient along the guide wire 338 and replaced with a separate catheter device (not shown). To this end, the catheter body 332 may be configured to provide a rapid exchange feature, as would be apparent to one of ordinary skill.

The pulmonary vein isolation catheter of the present invention, and in particular the substantially closed loop configuration, provides a highly viable tool for electrically isolating a vessel, such as a pulmonary vein, from a chamber, such as the left atrium. In this regard, the substantially closed loop is orientated transverse to a longitudinal axis of the catheter assembly so as to facilitate rapid, consistent placement of the ablation loop at a desired location along the left atrium or other chamber wall. This transverse orientation allows for guiding of the catheter assembly in a direction parallel to the axis defined by the vessel ostium, as opposed to a radial approach. Thus, the numerous complications presented by prior art sliding techniques are avoided. Further, due to this transverse orientation, the catheter assembly can further be provided with a locating device extending distal the ablation loop for easily locating a particular vessel, as well as to center the loop around the vessel ostium. Finally, the locating device can be provided with mapping electrodes such that mapping of the pulmonary vein in conjunction with ablation about the pulmonary vein ostium can be achieved with a unitary device.

Although the present invention has been described with reference to preferred embodiments, workers skilled in the art will recognize that changes may be made in form and detail without departing from the spirit and scope of the invention. For example, the preferred embodiment has described electrical isolation of a pulmonary vein from the left atrium for treatment of atrial fibrillation. Alternatively, the method and apparatus of the present invention may be utilized in the treatment of other cardiac arrhythmias, such as isolating the coronary sinus from the left atrium or isolating the outflow tract (or pulmonary valve) from the right ventricle. Further, a number of the described embodiments have included a catheter body forming a single loop. Alternatively, a multi-plane coil or spiral may be formed. The coil or spiral may increase or decrease in diameter as it extends distally, or may have a uniform diameter. Additionally, while the loop has been described as preferably being circular, a variety of other substantially closed shapes, including square, triangular, octagonal, etc. are equally acceptable. Also, several of the described embodiments have included a locating device for centering the loop about a pulmonary vein ostium and for mapping a pulmonary vein. In this regard, the locating device may be configured to serve only as a centering device or only as a mapping device, or both. Finally, other features may be incorporated into the catheter assembly. For example, to expedite deployment, the catheter assembly may be configured to slidably receive a guide wire used to position the catheter assembly within the left atrium. Even further, the catheter assembly may include a rapid exchange feature for quick placement over and removal from the guide wire.

What is claimed:

1. A catheter assembly for treatment of cardiac arrhythmia, the catheter assembly comprising:
   a catheter body having a proximal portion and a distal portion and defining a longitudinal axis;
   a wire basket connected to an exterior of the catheter body along the distal portion thereof, the wire basket being selectively transitionable between a retracted position and an expanded position; and
   a plurality of electrodes maintained by the wire basket; wherein the catheter assembly is configured such that in the expanded position, the wire basket positions the electrodes to define an ablation loop that is transverse to the longitudinal axis and adapted to encompass a pulmonary vein ostium, and further comprising a cooling source fluidly coupled to a portion of the wire basket.

2. The catheter assembly of claim 1, further comprising a plurality of wire struts each supporting at least one of the plurality of electrodes.

3. The catheter assembly of claim 2, wherein each of the wire struts is tubular.

4. The catheter assembly of claim 2, wherein at least one electrode associated with a respective wire strut is positioned distal a center point of the respective wire strut.

5. The catheter assembly of claim 2, wherein the expandable basket structure further includes a proximal collar and a distal collar coupling the wire struts to the catheter body.

6. The catheter assembly of claim 5, wherein the proximal collar is slidable relative to the distal collar so that the expandable basket structure expands when the proximal collar approaches the distal collar.

7. The catheter assembly of claim 1, further comprising a temperature sensing element operatively coupled to at least one of the wire struts.

8. The catheter assembly of claim 7, wherein the temperature sensing element is electrically coupled to provide closed loop feedback of the temperature of affected tissue dining an ablation procedure.

9. The catheter assembly of claim 7, wherein the temperature sensing element is integrated into one of the plurality of electrodes.

10. The catheter assembly of claim 1, further comprising:
    an elongated portion of the catheter assembly configured as a locating device disposed substantially in alignment with the center longitudinal axis and connected to the catheter body distal the expandable basket structure, the locating device adapted to center the ablation loop relative to an ostium.

11. A catheter assembly for treatment of cardiac arrhythmia, the catheter assembly comprising:
    a catheter body having a proximal portion and a distal portion and defining a central longitudinal axis;
    an expandable basket structure coupled around the catheter body and spaced from a distal end of the catheter body and wherein opposing ends of the expandable basket structure are coupled to the catheter body and an intermediate portion of the expandable basket structure is spaced from the catheter body and said intermediate portion being selectively circumferentially expanded and contracted between a retracted position and an expanded position relative to the central longitudinal axis; and
    a plurality of electrodes operatively coupled to the expandable basket structure;
    wherein the catheter assembly is configured such that in the expanded position, the expandable basket structure positions the electrodes to define an ablation loop that is transverse to the longitudinal axis and adapted to encompass a pulmonary vein ostium and wherein the ablation loop has a central loop axis aligned with the central longitudinal axis and further comprising an inflatable balloon coupled to the catheter body distal the expandable basket structure.

12. The catheter assembly of claim 11, wherein the ablation loop is adapted to ablate a lesion pattern about a pulmonary vein ostium upon activation of the electrodes.

13. The catheter assembly of claim 11, further comprising:
    a mapping electrode coupled to the catheter body and disposed distal the expandable basket structure.

14. A method for forming an ablation pattern to electrically isolate a vessel having an ostium from a cardiac chamber of a patient for treatment of a cardiac arrhythmia, the treatment comprising:
    providing a catheter assembly including a catheter body defining a longitudinal axis and having a proximal portion and a distal portion, a wire basket connected to an exterior of the catheter body along the distal portion thereof, and a plurality of electrodes maintained by a plurality of elongated members of the wire basket, the wire basket being selectively transitionable between a retracted position and an expanded position, wherein in the retracted position and in the expanded position the plurality of electrodes are substantially equally spaced from the longitudinal axis of the catheter body by a first common spacing and a second common spacing, respectively, and wherein the first common spacing is less than the second common spacing and the plurality of elongated members are substantially aligned with the longitudinal axis of the catheter body;

guiding the distal portion into the chamber with the wire basket in the retracted position;

transitioning the wire basket to the expanded position such that the electrodes are positioned to define an ablation loop;

aligning the longitudinal axis with the vessel ostium;

advancing the distal portion such that the ablation loop contacts the chamber wall about the vessel ostium; and energizing one or more of the electrodes to ablate a lesion pattern on the chamber wall about at least a portion of the vessel ostium to electrically isolate the vessel from the chamber.

15. The method of claim 14, wherein the chamber is a left atrium and the vessel is a pulmonary vein.

16. The method of claim 14, wherein the chamber is a right atrium and the vessel is a coronary sinus.

17. The method of claim 14, wherein transitioning the wire basket includes positioning the electrodes to define the ablation loop substantially transverse to the longitudinal axis.

18. The method of claim 17, wherein the ablation loop defines a central axis, and further wherein advancing the distal portion includes directing the distal portion in a direction parallel with the central axis.

19. The method of claim 14, wherein transitioning the wire basket includes forming the ablation loop to a size larger than a size of the vessel ostium.

20. The method of claim 14, wherein the wire basket includes proximal and distal collars connected to the catheter body, and further wherein transitioning the wire basket to the expanded position includes:

sliding at least one of the proximal and distal collars relative to an other of the proximal and distal collars.

21. The method of claim 20, wherein the proximal collar is slidable relative to the distal collar.

22. The method of claim 14, wherein the catheter assembly further includes a tip extending distal the wire basket, the method further including: locating the vessel with the tip.

23. The method of claim 22, wherein the tip further includes a centering device, the method further comprising:
centering the ablation loop about the vessel ostium via the centering device.

24. The method of claim 22, wherein the tip further includes at least one mapping electrode distal the wire basket, the method further including:
mapping tissue of the vessel with the mapping electrode.

25. A method for forming an ablation pattern to electrically isolate a vessel having an ostium from a chamber formed within a patient for treatment of cardiac arrhythmia, the treatment comprising:

providing a catheter assembly including a catheter body defining a longitudinal axis and having a proximal portion and a distal portion, a wire basket connected to an exterior of a catheter body along the distal portion thereof, and a plurality of electrodes maintained by the wire basket, the wire basket being selectively transitionable between a retracted position and an expanded position;

guiding the distal portion into the chamber with the wire basket in the retracted position;

transitioning the wire basket to the expanded position such that the electrodes are positioned to define an ablation loop;

aligning the longitudinal axis with the vessel ostium;

advancing the distal portion such that the ablation loop contacts the chamber wall about the vessel ostium;

energizing one or more of the electrodes to ablate a lesion pattern on the chamber wall about at least a portion of the vessel ostium to electrically isolate the vessel from the chamber wherein the wire basket is comprised of a plurality of tubular wire struts fluidly connected to a cooling source, and further comprising the step of:
initiating fluid flow from the cooling source to the tubular wire struts following the step of energizing one or more of the electrodes.

26. The method of claim 25, wherein the catheter assembly further includes at least one temperature sensing element coupled to a portion of the wire basket, the method further comprising: sensing a temperature at the chamber wall with the at feast one temperature sensing element following the step of energizing one or more of the electrodes.

* * * * *

UNITED STATES PATENT AND TRADEMARK OFFICE
CERTIFICATE OF CORRECTION

PATENT NO. : 6,572,612 B2
DATED : June 3, 2003
INVENTOR(S) : Mark T. Stewart et al.

It is certified that error appears in the above-identified patent and that said Letters Patent is hereby corrected as shown below:

Column 20,
Line 24, "with the central longitudinal" should read -- with the longitudinal --

Column 22,
Line 45, "at feast one" should read -- at least one --

Signed and Sealed this

Twenty-fifth Day of May, 2004

JON W. DUDAS
*Acting Director of the United States Patent and Trademark Office*